(12) United States Patent
Gilbert et al.

(10) Patent No.: US 7,736,572 B2
(45) Date of Patent: Jun. 15, 2010

(54) SYSTEM AND METHOD FOR AN EXPANDABLE PUSHROD MOLD SEAL

(75) Inventors: Steven Ray Gilbert, Fairfield, OH (US); Joseph Michael Manton, Cincinnati, OH (US); Mihai Alin Stan, Brussels (BE)

(73) Assignee: The Procter & Gamble Company, Cincinnati, OH (US)

( * ) Notice: Subject to any disclaimer, the term of this patent is extended or adjusted under 35 U.S.C. 154(b) by 756 days.

(21) Appl. No.: 11/595,322

(22) Filed: Nov. 10, 2006

(65) Prior Publication Data
US 2008/0110005 A1 May 15, 2008

(51) Int. Cl.
| | |
|---|---|
| B29C 59/02 | (2006.01) |
| B27N 3/18 | (2006.01) |
| B28B 3/00 | (2006.01) |
| B28B 3/02 | (2006.01) |
| B29C 41/46 | (2006.01) |
| B29C 43/02 | (2006.01) |
| B29C 43/32 | (2006.01) |
| B29C 51/00 | (2006.01) |
| B29D 17/00 | (2006.01) |
| D04H 1/20 | (2006.01) |
| B29C 41/00 | (2006.01) |
| B29C 61/00 | (2006.01) |

(52) U.S. Cl. .................... 264/320; 264/319; 264/107; 264/112; 264/230

(58) Field of Classification Search ......... 264/319–320, 264/107, 112, 230
See application file for complete search history.

(56) References Cited

U.S. PATENT DOCUMENTS

| 2,713,699 | A | * | 7/1955 | Pooley ..................... 264/54 |
| 3,875,615 | A | * | 4/1975 | Muckenfuhs ............. 28/119 |
| 6,682,513 | B2 | | 1/2004 | Agyapong et al. |
| 7,120,977 | B2 | | 10/2006 | Bittner et al. |
| 7,124,483 | B2 | | 10/2006 | Prosise et al. |
| 2004/0244165 | A1* | | 12/2004 | Bittner et al. ............ 28/118 |

OTHER PUBLICATIONS

U.S. Appl. No. 11/601,946, filed Nov. 20, 2006, Gilbert et al.

* cited by examiner

*Primary Examiner*—Khnh Nguyen
*Assistant Examiner*—Matthew Hoover
(74) *Attorney, Agent, or Firm*—James E. Oehlenschlager; David M. Weirich

(57) ABSTRACT

A process and apparatus for producing a stabilized product from a pledget, including the steps of providing a pledget, a transfer member having an expandable portion, and a stabilization mold having an interior surface defining an interior cavity. The pledget is pushed into the mold by the transfer member so that the expandable portion is within the interior cavity of the mold. The pledget is compressed in the mold by the transfer member to form a compressed pledget. The expandable portion of the transfer member is expanded to form a seal with the interior surface of said mold. The compressed pledget is stabilized to form a stabilized product, while the compressed pledget is maintained in compression and the expandable portion of the transfer member remains expanded.

20 Claims, 22 Drawing Sheets

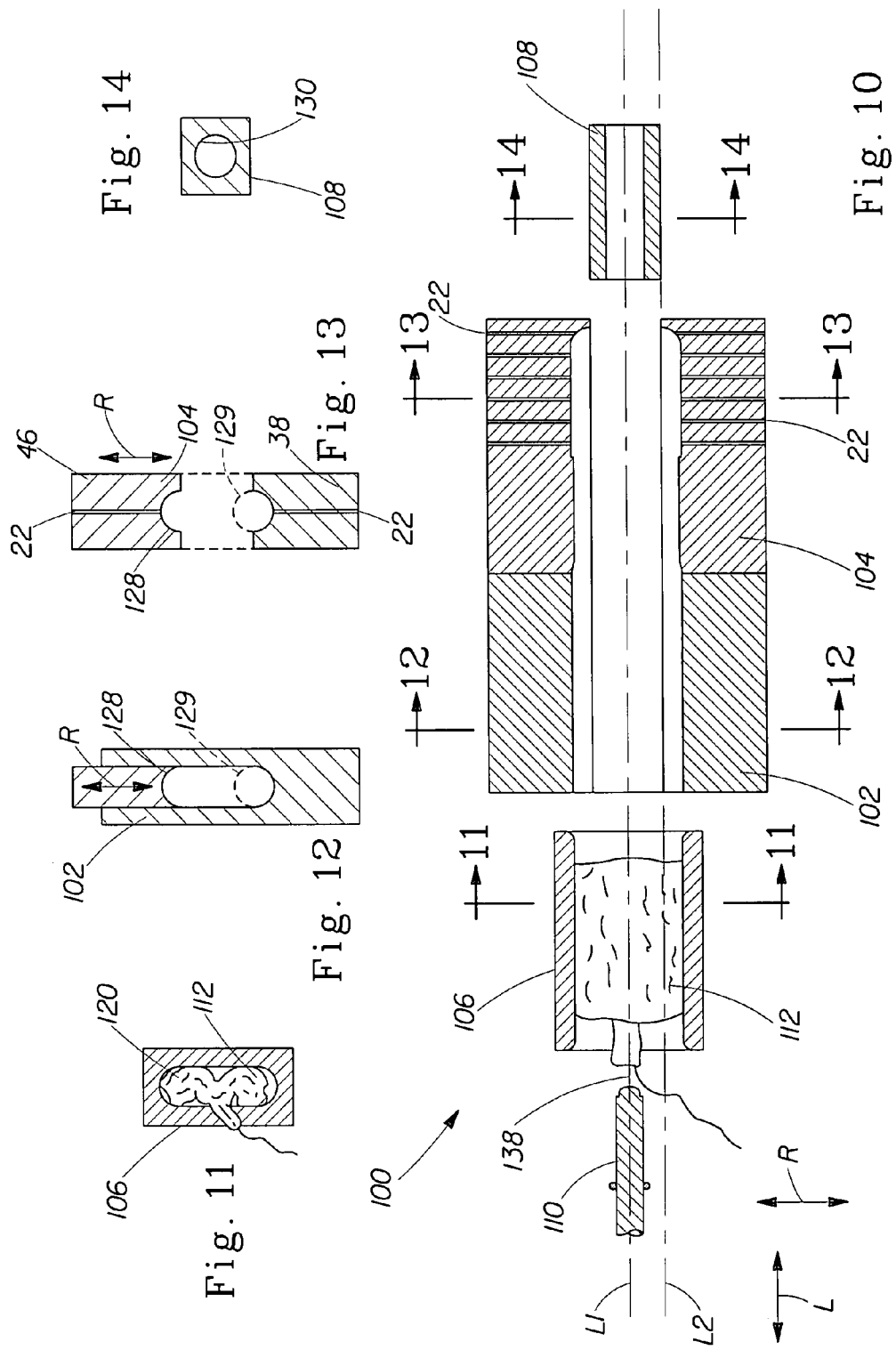

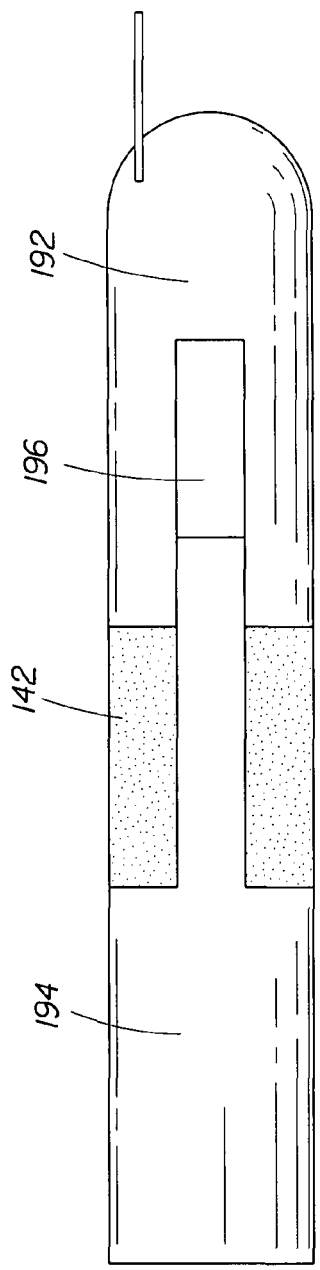
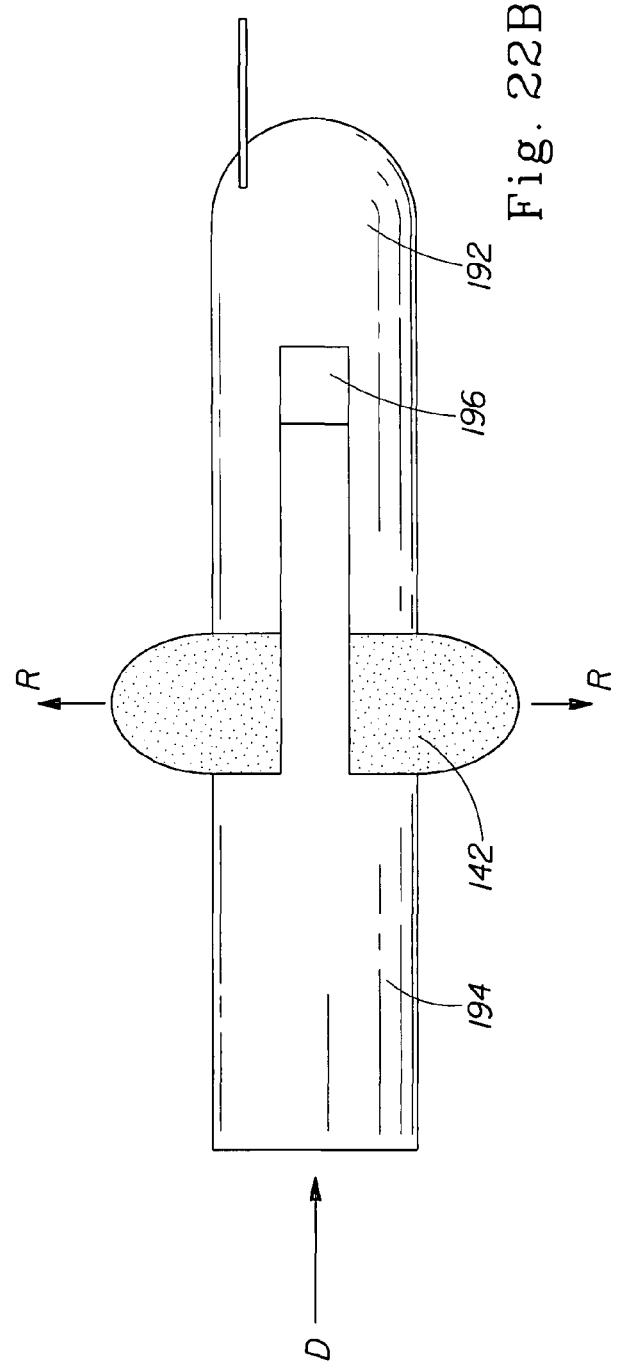

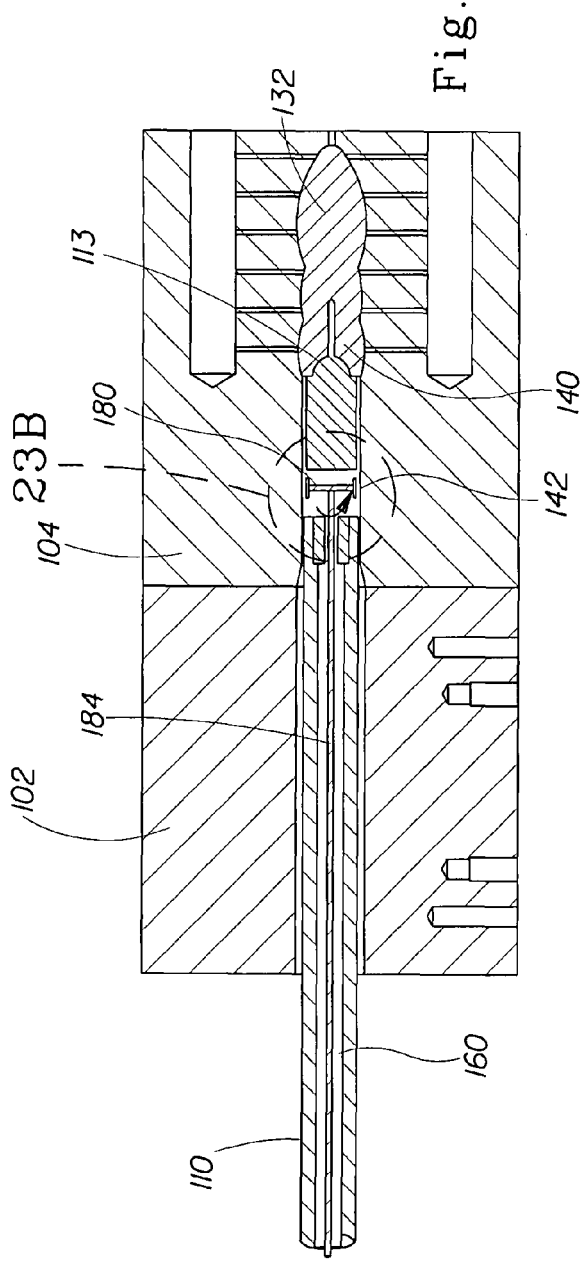

SYSTEM AND METHOD FOR AN EXPANDABLE PUSHROD MOLD SEAL

BACKGROUND OF THE INVENTION

Compressed products may be formed under sustained high pressure during their production. Compressed products also may be exposed to thermal molding conditions when formed. An enclosed mold is frequently used, with a pushrod that mechanically loads a pledget into the mold and sustains its holding force during heat treatments used to stabilize the pledget. To accelerate the thermal setting of the pledget, which provides stability to the final compressed product, steam heating may be employed due to its rapid heating characteristics.

However, steam may compromise the quality of the product's surface finish, the surrounding production equipment, and other products if the steam is not sufficiently contained in the mold when the heat treatment is applied. One source of this difficulty is the pushrod used for loading the pledget into the mold. The pushrod, which closes one end of the mold when the product is stabilized, may not create a complete seal.

The pushrod should force the pledget fiber into the mold and through other various components of the production equipment without shearing or damaging the product, its associated components such as cords, the mold surface, or even the pushrod itself. The pushrod also should prevent steam leaks from escaping the molding area, which may allow condensation of water to contaminate the tampon or the surrounding equipment.

The present invention solves the above-identified problems by supplying a pushrod that serves the sealing functions, but without damaging the product or production components.

BRIEF SUMMARY OF THE INVENTION

The invention relates to a process and apparatus for producing a stabilized product from a pledget, including the steps of providing a pledget, a transfer member having an expandable portion, and a stabilization mold having an interior surface defining an interior cavity. The pledget is pushed into the mold by the transfer member so that the expandable portion is within the interior cavity of the mold. The pledget is compressed in the mold by the transfer member to form a compressed pledget. The expandable portion of the transfer member is expanded to form a seal with the interior surface of the mold. The compressed pledget is stabilized to form a stabilized product, while the compressed pledget is maintained in compression and the expandable portion of the transfer member remains expanded.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying Figures, in which:

FIG. 10 is a simplified longitudinal cross-sectional view of one embodiment of the process of the present invention.

FIG. 11 is a simplified radial cross-sectional view of a pledget infeed carrier of FIG. 10, taken along line 11-11.

FIG. 12 is a simplified radial cross-sectional view of the split compression mold of FIG. 10, taken along line 12-12.

FIG. 13 is a simplified radial cross-sectional view of the split stabilization mold of FIG. 10, taken along line 13-13.

FIG. 14 is a simplified radial cross-sectional view of a discharge carrier of FIG. 10, taken along line 14-14.

FIG. 22A is a cross-sectional view of another embodiment of the transfer member with an expandable seal in a relaxed position.

FIG. 22B is a cross-sectional view of the transfer member shown in FIG. 22A with the expandable seal in an expanded position.

FIG. 23A is a cross-sectional view of a stabilization mold and a transfer member with an expansion plate in a closed position in another embodiment where the seal is expanded mechanically.

FIG. 23B is a cross-sectional view of the embodiment of the transfer member shown in FIG. 23A, where the expansion plate is in a closed position.

FIG. 23C is a cross-sectional view of the embodiment of the transfer member shown in FIG. 23A, where the expansion plate is in an open position.

FIG. 23D is a top view of the embodiment of the expansion plate shown in FIG. 23C, where the expansion plate is in an open position.

DETAILED DESCRIPTION OF THE INVENTION

As used herein, the term "pledget" refers to a construction of absorbent material prior to the compression of such construction into a tampon or other absorbent product. The pledget and compressed product may be a tampon, including nosepacks, a tampon used to absorb menses or other feminine hygiene products, incontinence articles, bandages, or any other compressed absorbent product. Where the term "tampon" is used herein, that usage is for illustrative purposes only, and is not to be construed as limiting.

As used herein, "compression" refers to the process of pressing, squeezing, compacting, or otherwise manipulating the size, shape, and/or volume of a material to obtain a compressed pledget having a suitable shape. Where the product is a compressed tampon pledget, the shape may be a vaginally insertable shape. The term "compressed" refers to the state of a material or materials subsequent to compression. Conversely, the term "uncompressed" refers to the state of a material or materials prior to compression. The term "compressible" is the ability of a material to undergo compression.

The term "joined" or "attached," as used herein, encompasses configurations in which a first element is directly secured to a second element by affixing the first element directly to the second element; configurations in which the first element is indirectly secured to the second element by affixing the first element to intermediate member(s) which in turn are affixed to the second element; and configurations in which the first element is integral with the second element; i.e., the first element is essentially part of the second element.

Figure 1:
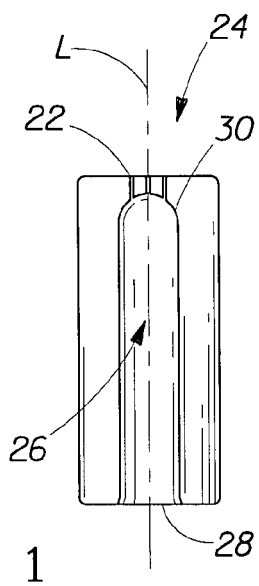
FIG. 1 is a cross section of a unitary embodiment of a permeable mold with pores located axially along the mold.
Figure 2:
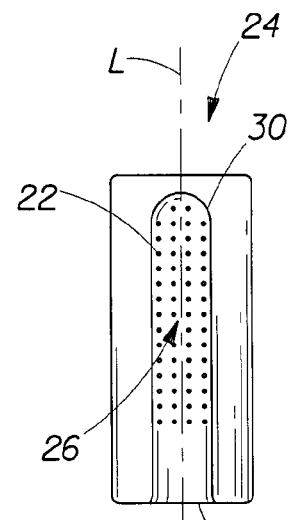
FIG. 2 is a cross section of a unitary embodiment of a permeable mold with pores located radially along the mold.

As used herein, "mold" refers to a structure for shaping a pledget during compression and/or retaining the shape for a compressed tampon pledget subsequent to compression during the stabilization process. Molds have an inner surface defining an inner cavity and an outer surface. The inner cavity is structured to define or mirror the shape of the pledget or the compressed tampon pledget. Thus, in some embodiments the pledget conforms to the shape of the inner cavity of the mold by a restraining force to result in a self-sustaining shape, and is retained in the inner cavity during the stabilization process. In other embodiments, the mold retains the shape of the compressed tampon pledget during the stabilization process. The inner cavity may be profiled to achieve any shape known in the art including, but not limited to, cylindrical, rectangular, triangular, trapezoidal, semi-circular, hourglass, serpentine, or other suitable shapes. The outer surface of the mold is the surface external to the inner surface and can be profiled or shaped in any manner, such as rectangular, cylindrical, or oblong. The mold may comprise one or more members. One mold used in the present invention may be a unitary mold, comprising one member, as shown in FIGS. 1 and 2, or a "split cavity mold," as shown in FIG. 3, FIG. 4, FIG. 5, FIG. 6, and FIG. 7. Split cavity molds may be used when producing shaped tampons, such as those disclosed in U.S. Pat. Nos. 6,824,536 and 6,932,805. Unitary molds may be used for less complex shapes such as cylindrical or substantial cylindrical.

The term "permeable," as used herein, refers to the ability of a material to allow the spread or infusion of a gas, a liquid, or a evaporative material through the material's composition. It is to be understood that "gas," as used in this document, refers to any suitable substance, including those in gaseous, liquid, or evaporative forms. A material may be permeable due to its composition or the material may be fabricated from impermeable material modified to become permeable, either chemically, mechanically, or electrically, such as, for example, by acid etching, drilling, or aperturing.

The term "pores," as used herein, refers to small openings or interstices that connect the inner surface of the mold with the outer surface of the mold, admitting the passage and infusion of gases into and through a compressed tampon pledget contained within the inner cavity of the mold.

As used herein, "self-sustaining" is a measure of the degree or sufficiency to which an absorbent material, such as a tampon or other absorbent product, retains its compressed form after stabilization, such that, in the absence of external forces, the resulting product will tend to retain its shape and size. For tampons, it is found that control of the level of moisture within the tampon is a factor for helping the tampon to retain its vaginally insertable shape and size subsequent the absence of the external compression forces. It will be understood by one of skill in the art that this self-sustaining form need not persist during actual use of the tampon. That is, once the tampon is inserted into the vagina or other body cavity and/or begins to acquire fluid, the tampon may expand and lose its self-sustaining form.

The term "shaped tampons," as used herein, refers to compressed tampon pledgets having either a substantially serpentine shape, or an "undercut" or "waist." The phrase "substantially serpentine" refers to a non-linear dimension between any two points spaced at least about 5 mm apart. The term "undercut" refers to tampons having a protuberance or indentation that impedes the withdrawal from a unitary mold. For example, shaped tampons may be hourglass shaped having at least one perimeter in the center of the tampon or "waist" that is less than both an insertion end perimeter and a withdrawal end perimeter.

As used herein, the term "split cavity mold" is a mold comprised of two or more members that, when brought together, complete the inner cavity of the mold. Each member of the split cavity mold comprises at least a portion of the inner surface that when brought together or closed completes the mold structure. The split cavity mold is designed such that at least two or more of the mold members can be at least partially separated, if not fully separated, typically after the tampon has acquired a self-sustaining shape, to expand the cavity volume circumscribed by the inner surface(s), thus permitting the easier removal of the tampon from the mold. Where each member's inner surface portion joins the inner surface portion of another member, those points of adjacency can define a straight line, a curve, or another seam of any convoluted intersection or seam of any regular or irregular form. The elements of the split cavity in some embodiments may be held in appropriate position relative to each other by linking elements of any form including bars, rods, linked cams, chains, cables, wires, wedges, screws, etc.

The term "stabilized," as used herein, refers to a tampon in a self-sustaining state, wherein it has overcome the natural tendency to re-expand to the original size, shape, and volume of the absorbent material and overwrap, which comprise the pledget.

As used herein, the terms "tampon" or "stabilized tampon" refer to any type of absorbent structure that is inserted into the vaginal canal or other body cavities for the absorption of fluid therefrom, to aid in wound healing, or for the delivery of active materials, such as medicaments, or moisture. Other absorbent products or portions thereof may also be formed and stabilized through the processes described herein, including without limitation, sanitary napkins, wipes, cleaning products, diapers, makeup applicators, makeup removers, sponges, and other products that expand. The tampon, or other absorbent product, may be compressed into a generally cylindrical configuration in the radial direction, axially along the longitudinal axis, or in both the radial and axial directions. While the tampon may be compressed into a substantially cylindrical configuration, other shapes are possible. These may include shapes having a cross section that may be described as rectangular, triangular, trapezoidal, semi-circular, hourglass, serpentine, or other suitable shapes. Tampons have an insertion end, withdrawal end, a length, a width, a longitudinal axis, and a radial axis. The tampon's length can be measured from the insertion end to the withdrawal end along the longitudinal axis. A typical tampon for human use is about 30-60 mm in length. A tampon may be straight or non-linear in shape, such as curved along the longitudinal axis. A typical tampon is about 8-20 mm wide. The width of a tampon, unless otherwise stated in the specification, corresponds to the length across the largest cylindrical cross-section, along the length of the tampon.

The term "vaginal cavity," "within the vagina," and "vaginal interior," as used herein, are intended to be synonymous, and refer to the internal genitalia of the mammalian female in the pudendal region of the body. The term "vaginal cavity" as used herein is intended to refer to the space located between the introitus of the vagina (sometimes referred to as the sphincter of the vagina or hymeneal ring) and the cervix. The terms "vaginal cavity," "within the vagina," and "vaginal interior" do not include the interlabial space, the floor of vestibule, or the externally visible genitalia.

As used herein, "cm" is centimeter, "g" is grams, "g/m$^2$" is grams per meter squared, "L" is liters, "L/s" is liters per second, "mL" is milliliters", "mm" is millimeters, "min" is minutes, "rpm" rate per minute, and "s" is seconds.

FIG. 1 and FIG. 2 show cross sections of a unitary embodiment of the permeable mold with a longitudinal axis L. The structure of the unitary mold 24 is a one piece mold so arranged as to define a space or inner cavity 26 for shaping a pledget during compression and/or retaining the shape for a compressed pledget subsequent to compression during the stabilization process. The inner cavity 26 has an open proximal end 28 and a closed distal end 30. In the unitary embodiments of the permeable mold, the open proximal end 28 may be used for both an ingress port where the pledget is introduced into the inner cavity 26 and an egress port where the final compressed product can be extracted from the inner cavity 26. In the embodiment shown in FIG. 1, the unitary mold 24 has pores 22 located axially along the unitary mold 24, the pores 22 being shown at the closed distal end 30. As shown in FIG. 2, the unitary mold 24 has pores 22 located radially along the unitary mold 24.

Figure 3:
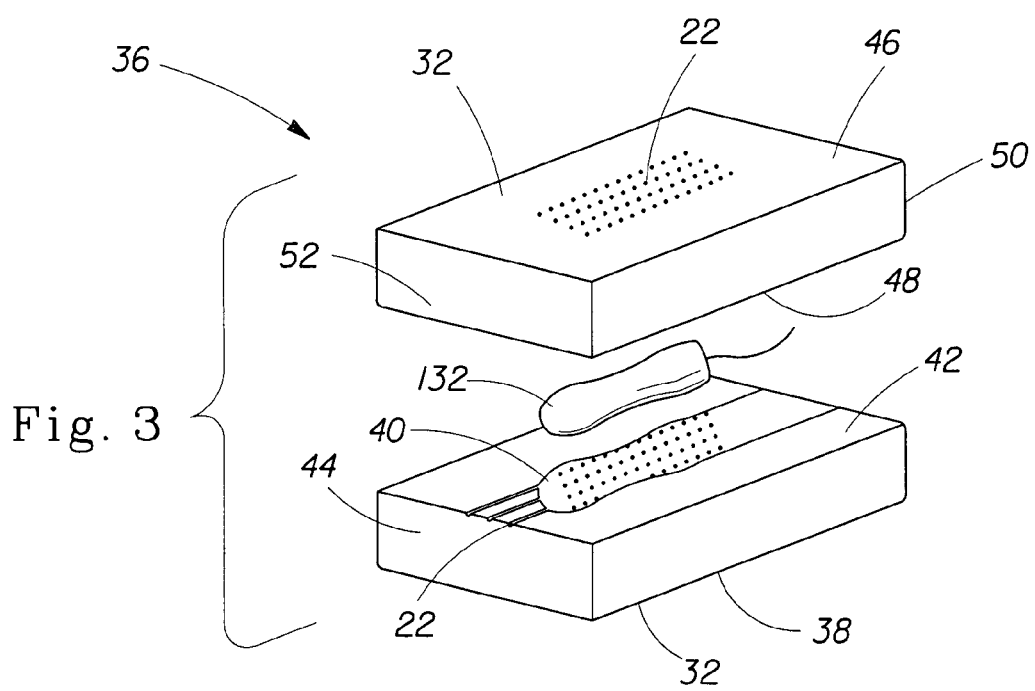
FIG. 3 is an exploded view of a split cavity mold with the compressed pledget positioned between the first split cavity mold member and the second split cavity mold member.

FIG. 3 shows an exploded view of an example of a split cavity mold 36 with a compressed pledget 132 positioned between first split cavity mold member 38 and second split cavity mold member 46. The first split cavity mold member 38 and second split cavity mold member 46 are combined to form a split cavity mold 36. The first split cavity mold member 38 has a first inner surface 40 and an outer mold surface 32. The second split cavity mold member 46 is substantially similar, if not a mirror image or not identical in size, shape, and dimension, to the first split cavity mold member 28, and has a second inner surface 48 and an outer mold surface 32. The first split cavity mold member 38 and the second split cavity mold member 46 are configured such that the first end 42 and the second end 44 of the first split cavity mold member 38 corresponds to the first end 50 and the second end 52 of the second split cavity mold member 46, such that the first inner surface 40 and the second inner surface 48 face toward each other. These inner surfaces make up an inner cavity that is the desired shape of the compressed pledget. In the embodiment shown, both the first split cavity mold member 38 and the second split cavity mold member 46 have pores 22 located axially and radially along the mold.

The mold can be constructed from permeable materials or can be fabricated from impermeable or permeable materials, and modified either mechanically, chemically, electrically, or a combination of the above to become permeable. Materials for the mold may include metals, polymers, composites, any other suitable material, or combinations of the above. Embodiments of the mold that are comprised of metals may include steel, stainless steel, copper, brass, titanium, alloys, aluminum, anodized aluminum, titanium, and combinations thereof. Embodiments of the mold that are comprised of polymers may include TEFLON® (E.I du Pont de Nemours and Company), polyethylene, polypropylene, polyester, polyolefins, polycarbonates, nylons, polyvinyl chloride, and mixtures thereof. One embodiment of a mold may be made of DELRIN® made by DuPont Plastics. Embodiments of the mold that are comprised of composites may include carbon fibers and blends of metal, epoxy, ceramic, and polymer blends. Other examples of suitable materials for the mold are foamed metals or plastics. The mold may be made of aluminum and epoxy porous aggregate, such as METAPOR BF100A1, available from Portec Ltd, Switzerland. Pores, interstices, or pathways can be produced in the above materials by any suitable operation, including, but not limited to, operations such as drilling, milling, punching, casting, injection molding, acid etching, electrical discharge machining, or any other suitable method.

In various embodiments used with the process of the present invention, the pledget is maintained within a mold that comprises at least one pore along the length of the mold. The mold may have a plurality of pores in some embodiments. The pores can be on any location on the mold. In embodiments in which the mold is cylindrical, the pores may be located radially, axially, or both radially and axially. These pores may be macroscopic, microscopic, or submicroscopic. The pores may be of any suitable dimension. In some embodiments, the pores may range in diameter from about 0.2 mm to about 1.5 mm.

The process of the present invention may be used for stabilizing any type of tampon, including but not limited to the tampon disclosed in U.S. Pat. No. 6,258,075 and the shaped tampons disclosed in U.S. Pat. Nos. 6,824,536 and 6,932,805. Further, the process of the present invention may be used for the tampons having secondary absorbent members, disclosed in U.S. Publication No. 2005/0055003A1.

The absorbent material that comprises the pledgets may be constructed from a wide variety of liquid-absorbing materials suitable for absorbent articles. Such materials include but are not limited to rayon (such as GALAXY Rayon and SARILLE L rayon, both available from Kelheim Fibres, GmbH, of Kelheim, Germany), cotton, folded tissues, woven materials, nonwoven webs, synthetic and/or natural fibers or sheeting, comminuted wood pulp which is generally referred to as airfelt, other suitable materials, or combinations of these materials. Other materials that may be incorporated into the pledget including peat moss, absorbent foams (such as those disclosed in U.S. Pat. Nos. 3,994,298 and 5,795,921), capillary channel fibers (such as those disclosed in U.S. Pat. No. 5,356,405), high capacity fibers (such as those disclosed in U.S. Pat. No. 4,044,766), superabsorbent polymers or absorbent gelling materials (such as those disclosed in U.S. Pat. No. 5,830,543), other suitable materials, and combinations of these. A more detailed description of liquid-absorbing materials shapes and dimensions can be found in U.S. Pat. No. 6,740,070.

The compressed product stabilized by the process of the present invention may optionally include an overwrap comprising material such as, rayon, cotton, bicomponent fibers, polyethylene, polypropylene, other suitable natural or synthetic fibers known in the art, and mixtures thereof. In some embodiments, the tampon may include a nonwoven overwrap comprised of bicomponent fibers that have a polypropylene core surrounded by polyethylene manufactured by Vliesstoff-werke Christian Heinrich Sandler GmbH & Co. KG (Schwarzenbach/Saale, Germany) under the tradename SAS B31812000. In other embodiments, the tampon may comprise a nonwoven overwrap of a hydroentangled blend of 50% rayon, 50% polyester available as BBA 140027 produced by BBA Corporation of South Carolina, U.S. The overwraps may be treated to be hydrophilic, hydrophobic, wicking or non-wicking.

The compressed product stabilized by the process of the present invention may optionally include a withdrawal cord, a secondary absorbent member, an additional overwrap, a skirt portion, and/or an applicator. Withdrawal cords useful in the present invention may be made of any suitable material known in the prior art and include cotton and rayon. U.S. Pat. No. 6,258,075 describes a variety of secondary absorbent members for use in the products. An example of a skirt portion is disclosed in U.S. Pat. No. 6,840,927.

Pressures and temperatures suitable for compression may be used. Typically, the absorbent material and the overwrap are compressed in the radial direction and optionally axially by any suitable means.

The compressed product stabilized by the present invention may be inserted digitally, or insertion may be aided through the use of any suitable applicator. When tampons or other products are to be digitally inserted, it may be desirable to provide a finger indent made using a compression rod at the withdrawal end of the product to aid in insertion. An example of a finger indent in a tampon is found in U.S. Pat. No. 6,283,952. Applicators that may be used are "tube and plunger" or "compact" type arrangements and may be plastic, paper, or other suitable material.

Figure 4:
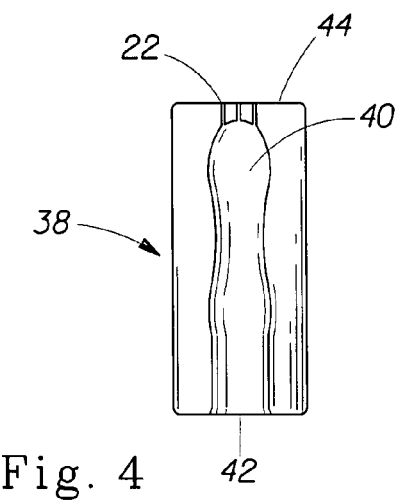
FIG. 4 is a plan view of a first split cavity mold member with pores located axially along the mold.
Figure 5:
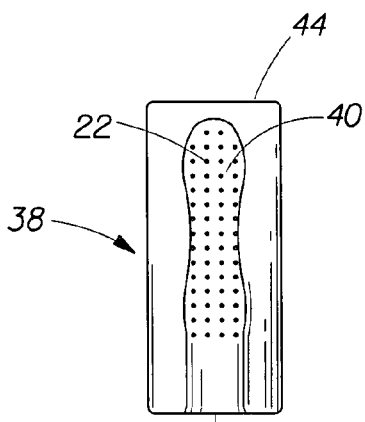
FIG. 5 is a plan view of a first split cavity mold member with pores located radially along the mold.

FIG. 4 and FIG. 5 show plan views of a first split cavity mold member 38 having a first inner surface 40. The first split cavity mold member 38 has a first end 42 and a second end 44. In the embodiment shown in FIG. 4, the first split cavity mold member 38 has pores 22 located axially along the first split cavity mold member 38. In the embodiment shown in FIG. 5, the first split cavity mold member 38 has pores 22 located radially along the first split cavity mold member 38.

Figure 6:
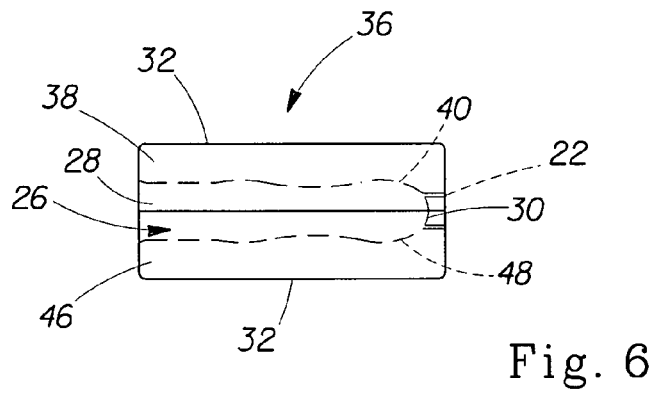
FIG. 6 is a side view of a split cavity mold with pores located axially along the mold.
Figure 7:
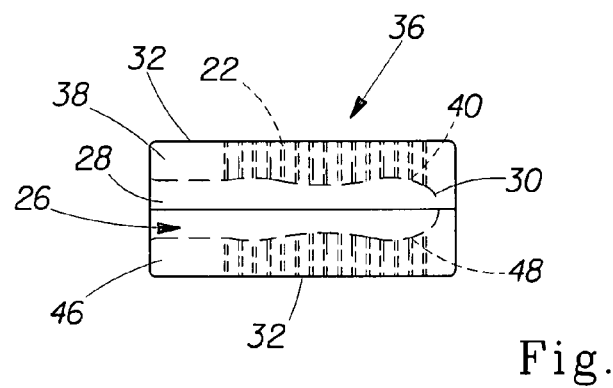
FIG. 7 is a side view of a split cavity mold with pores located radially along the mold.

FIG. 6 and FIG. 7 show a side view of the split cavity mold 36. The first split cavity mold member 38 and second split cavity mold member 46 are combined to form a split cavity mold 36. The first split cavity mold member 38 has a first inner surface 40 and an outer mold surface 32. The second split cavity mold member 46 is substantially similar, if not a mirror image or not identical in size, shape, and dimension, to the first split cavity mold member 38, and has a second inner surface 48 and an outer mold surface 32. The first split cavity mold member 38 and the second split cavity mold member 46 are configured such that the first inner surface 40 and the second inner surface 48 face each other and define an inner cavity 26 for shaping a pledget during compression, and/or retaining the shape for a compressed pledget subsequent to compression during the stabilization process. The inner cavity 26 has an open proximal end 28 and a closed distal end 30. In some embodiments, such as embodiments that combine compression and stabilization, the open proximal end 28 may act as an ingress port wherein the pledget is introduced in the inner cavity. In the embodiment shown in FIG. 6, the split cavity mold 36 has pores 22 located axially, or entering along the axis of the lengthwise axis of the compressed pledget, along the split cavity mold 36. In the embodiment shown in FIG. 7, the split cavity mold 36 has pores 22 located radially, or entering generally perpendicularly to the lengthwise axis of the compressed pledget, along the split cavity mold 36.

Figure 8:
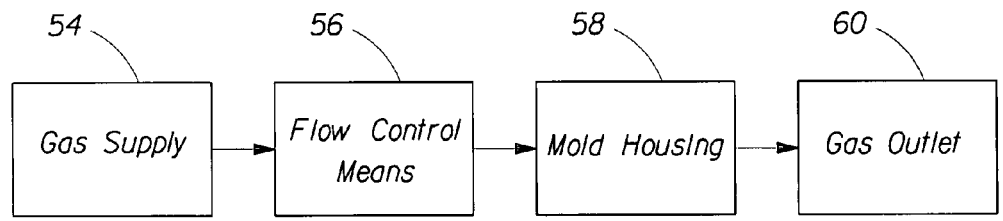
FIG. 8 is a diagram of one embodiment of a gas supply system in the process of the present invention.
Figure 9:
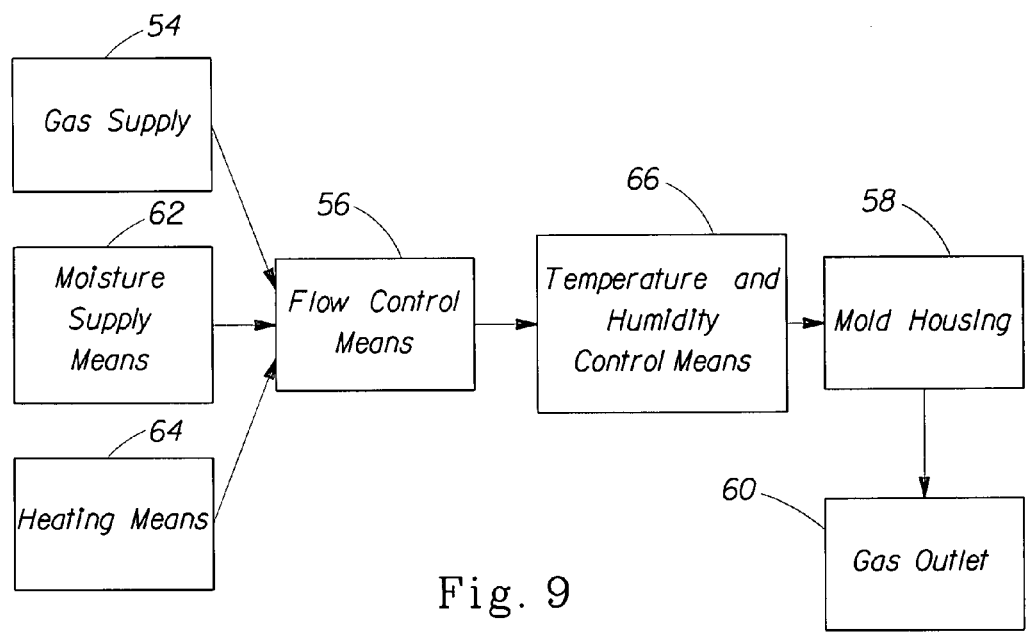
FIG. 9 is a diagram of another embodiment of a gas supply system of the process of the present invention.

FIG. 8 and FIG. 9 show a flow diagram of a process for using steam to stabilize the compressed pledget that may be used with the present invention. The process may comprise the steps of providing a compressed pledget and forcing gas through the compressed pledget. The compressed pledget may be maintained within a permeable mold during this process. In some embodiments of the process, the stabilized product may be produced in the presence of moisture. The moisture that is required in the process may be from the fibers of the material that comprises the pledget, within the gas that is introduced in the process, or both. In another embodiment of the process, the stabilization process may be combined with a compression process.

Any suitable targeted moisture content of the pledget after the stabilization process may be used. For example, the targeted moisture content may be from about 4% to about 15% of water by weight or any number within this range, or from about 8% to about 10% water by weight or any number within this range, as measured by the TAPPI method T 412.

The diagram in FIG. 8 shows that, in some embodiments, the process can be accomplished by providing a gas supply 54 opposed to a gas outlet 60, and a mold housing 58 oriented therebetween that contains the compressed tampon pledget within the permeable mold. The incoming gas enters the machine at the gas supply 54. The rate of the gas flow can be varied by a flow control means 56.

The gases forced into the compressed pledget may be air, oxygen, nitrogen, argon, carbon dioxide, steam, ether, freon, inert gases, other suitable gases, and mixtures thereof. The supply of the gas may be varied by a flow control means 56. During the process of the present invention the gas may be propelled through the mold at any suitable rate, including at a rate of from about 0.2 to about 5.0 L/s. In some embodiments, the gas is propelled for a time period ranging from about 1 s to about 20 s. In other embodiments, the gas is propelled for a time period ranging from about 1 s to about 10 s. In other embodiments, the gas is propelled from about 2 s to 8 s.

The process of the present invention may comprise the step of heating the gas that is introduced to the compressed pledget. The process of the present invention may comprise the step of humidifying the gas that is introduced to the compressed pledget. As shown in FIG. 9, a moisture supply means 62, heating means 64, and a temperature and humidity control means 66 is added to the diagram of FIG. 8. As such, the heated and humidified gas flows into the mold housing 58 oriented therebetween that contains the compressed pledget within the permeable mold and flows out the gas outlet 60.

In embodiments of the process where the gas is heated, a heating means 64 may be used. The temperature may be varied by the temperature and humidity control means 66. In some embodiments, the gas is heated to a range of about 60° C. to about 210° C. In some embodiments, the gas may be heated to about 100° C., and in other embodiments the gas may be heated to about 163° C. In embodiments where the compressed pledget is maintained in a permeable mold, the molds may be heated prior to insertion of the pledget into the mold. The molds may be heated prior to insertion of the pledget by hot air or alternate means, such as by conductive heating prior to insertion of the pledget. The mold can be heated from about 38° C. to about 210° C. In some embodiments, the molds may be heated to about 71° C. In some embodiments, the process also may comprise the step of cooling the product. In some embodiments, the product may be cooled by air to ambient room temperatures from about 21 to about 24° C., or any suitable temperature within this range, or less than about 30° C.

In embodiments of the process where the gas is humidified, the moisture may be added via a moisture supply means 62. The humidity can be varied by a temperature and humidity control means 66. The moisture or humidity in the gas may be introduced by any suitable method, including but not limited to atomization, evaporation, steam blending, super heated steam blending, supersaturated steam blending, other suitable methods, or the like. The gas may be humidified to a range from about 1% to about 100% relative humidity, or any suitable number within this range, at the gas temperature.

FIG. 10 is a simplified longitudinal cross-sectional view of one embodiment 100 of the process of the present invention, including a pair of split molds: a compression mold 102 and a stabilization mold 104. The embodiment 100 is suitable for mass-production of stabilized tampons or other products, wherein the steps of compressing and stabilizing the pledgets may be separated in order to reduce the complexity of the apparatus producing stabilized products, including products having a substantially serpentine shape and/or stabilized by the use of a gas.

Both the compression mold 102 and the stabilization mold 104 are shown in their open positions 128 and aligned with a pledget infeed carrier 106 and a product discharge carrier 108.

The embodiment 100 of FIG. 10 also shows a transfer member 110, or "pushrod," and a pledget 112 disposed in the pledget infeed carrier 106. The transfer member 110 can serve several functions: (a) transferring the pledget 112 through the sequence of process steps taking place during traveling of the pledget 112 from the pledget infeed carrier 106 to the compression mold 102, to the stabilization mold 104, and to the product discharge carrier 108; (b) compressing the pledget 112 longitudinally (in addition to the compression in the radial direction provided by the compression die 102, as described below); (c) forming a desired shape cavity at the base region of the product, suitable for the user's finger to facilitate digital insertion of the product into the vaginal (or other) cavity; and (d) providing a suitable seal for containing the gas inside the stabilizing die 104 during the stabilization treatment of the product, as described below.

The transfer member 110 may include at least one needle 138 extending from the transfer member 110 longitudinally for discharging a stabilized product from the split stabilization mold 104, as will be described in more detail below.

As shown in FIG. 10, the transfer member 110 may be aligned with the pledget infeed carrier 106, the compression mold 102, the stabilization mold 104, and the product discharge carrier 108 along a first longitudinal centerline L1.

It should be noted that the pledget having a secondary absorbent member extending from the base region of the pledget may be loaded into the pledget infeed carrier with the secondary absorbent member being diverted radially in relation to the pledget to ensure that the secondary absorbent member does not interfere with the movement of the transfer member 110. This reduces or prevents pushing the secondary absorbent member into the base region of the pledget. The radial diversion of the secondary absorbent member (including with at least one cord extending also from the base region of the product) can be provided during loading of the pledget by any suitable means, for example, a plate disposed in the direction of loading of the pledget into the cavity of the infeed carrier.

FIG. 11 is a simplified radial cross-sectional view of the pledget infeed carrier 106 of FIG. 10, taken along line 11-11. The pledget infeed carrier 106 includes a cavity 120 that can be suitably shaped to accept the pledget 112, which is shown as being folded to form an M-shape configuration. However, alternatively, the pledget 112 can be not folded or folded into any suitable configuration. The pledget infeed carrier 106 can be made from any material suitable for producing products according to the present invention.

FIG. 12 is a simplified radial cross-sectional view of the split compression mold 102 of FIG. 10, taken along line 12-12. The split compression mold 102 includes a first member 122 and a second member 124. At least one of the members 122 and 124 is capable of moving in a direction R to effect an open position 128 or a closed position 129 (shown as an interrupted line) of the split compression mold 102. In the closed position 129, the inner surface 127 of the compression mold 102 forms a cross-section of any desired shape, such as a generally circular cross-section of a desired diameter, for example, a diameter D of about 12.5 mm. The inner surface 127 can be of any suitable shape and of any desired dimension. The split compression mold 102 can be made from any materials capable of providing desired compression forces and suitable for producing products in accordance with the present invention.

FIG. 13 is a simplified radial cross-sectional view of the split stabilization mold 104 of FIG. 10, taken along line 13-13. The split stabilization mold 104 can be similar in the dimensions and makeup, in all or any aspects, to the split mold 36 shown in FIGS. 3-7 and described in more detail above. For example, similarly to the split mold 36 of FIGS. 3-7, the split stabilization mold 104 includes the first member 38, the second member 46, and at least one pore 22 suitable for providing a gas flow inside the inner surface of the stabilization mold 104. The split stabilization mold 104 is shown in the open position 128 when the first member 38 and the second member 46 are separated from each other. At least one of the mold members 38 and 46 can move in the direction R to effect the open position 128 or the closed position 129 (shown as an interrupted line) when the first member 38 and the second member 46 are in contact with each other.

FIG. 14 is a simplified radial cross-sectional view of a product discharge carrier 108 of FIG. 10, taken along line 14-14. The product discharge carrier 108 includes a cavity 130 that can be suitably dimensioned and shaped to accept the stabilized product.

In one embodiment of the present invention, the cavity 130 may be defined by a multiplicity of longitudinal flutes 133 to facilitate the dissipation of a gas forced into the cavity 130 during the stabilization process of the present invention. The product discharge carrier 108 can be made from any material suitable for producing products in accordance with the present invention.

Figure 15:
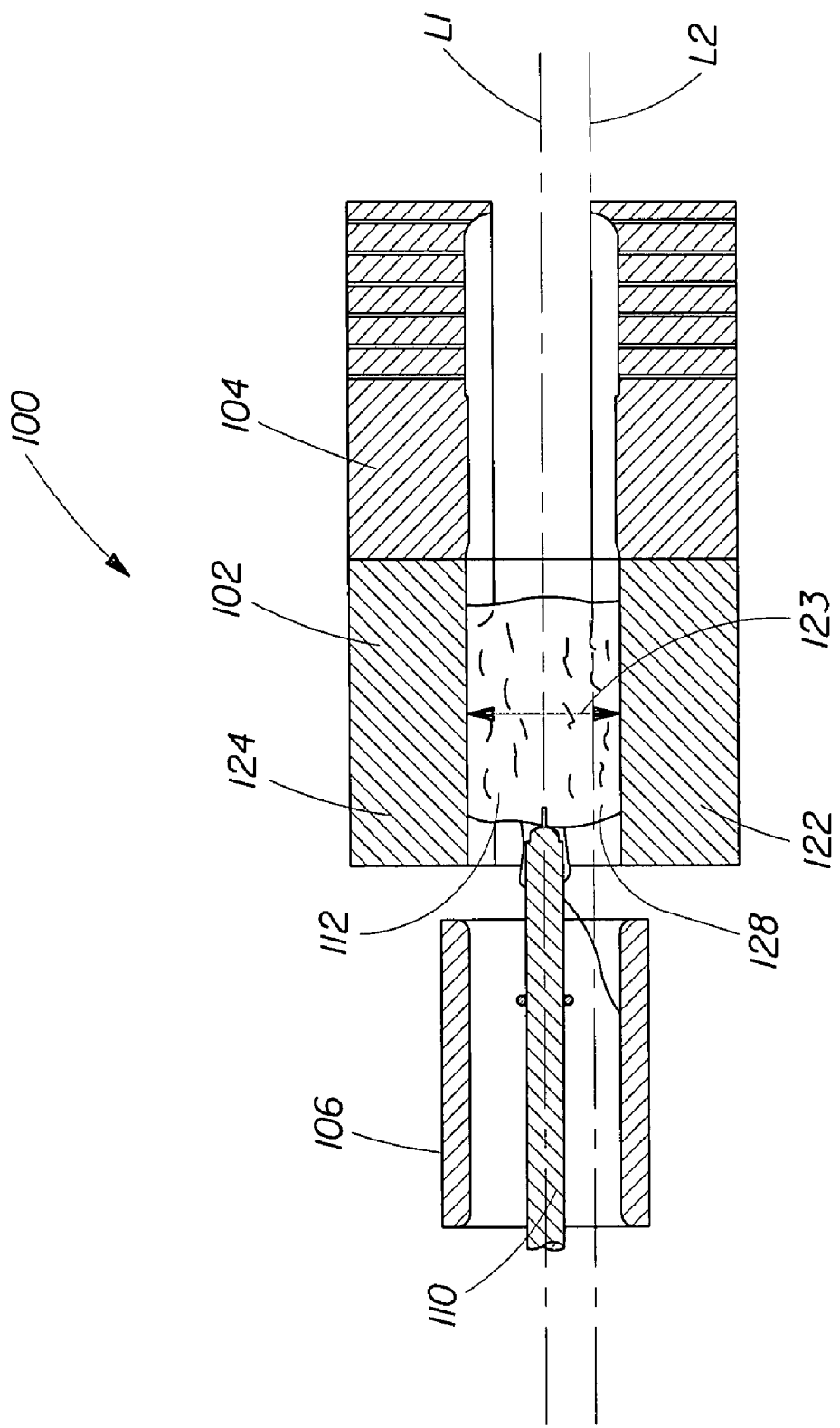
FIG. 15 is a simplified longitudinal cross-sectional view of the embodiment 100 of FIG. 10, showing a pledget being loaded into the split compression mold by a transfer member, the split compression mold being in an open position.

FIG. 15 is a simplified longitudinal cross-sectional view of the embodiment 100 of FIG. 10, showing the pledget 112 being loaded into the split compression mold 102 by the transfer member 110 when the split compression mold 102 is in the open position 128 and the transfer member 110 is aligned with the first longitudinal centerline L1. In the open position 128, the compression mold 102 has an inside dimension 123 that can be any dimension suitable for accepting the pledget 112. For example, in one embodiment of the invention, the inside dimension 123 may be from about 25 mm to about 80 mm, or any number in this range. In another embodiment, the inside dimension 123 is about 40.5 mm.

Figure 16:
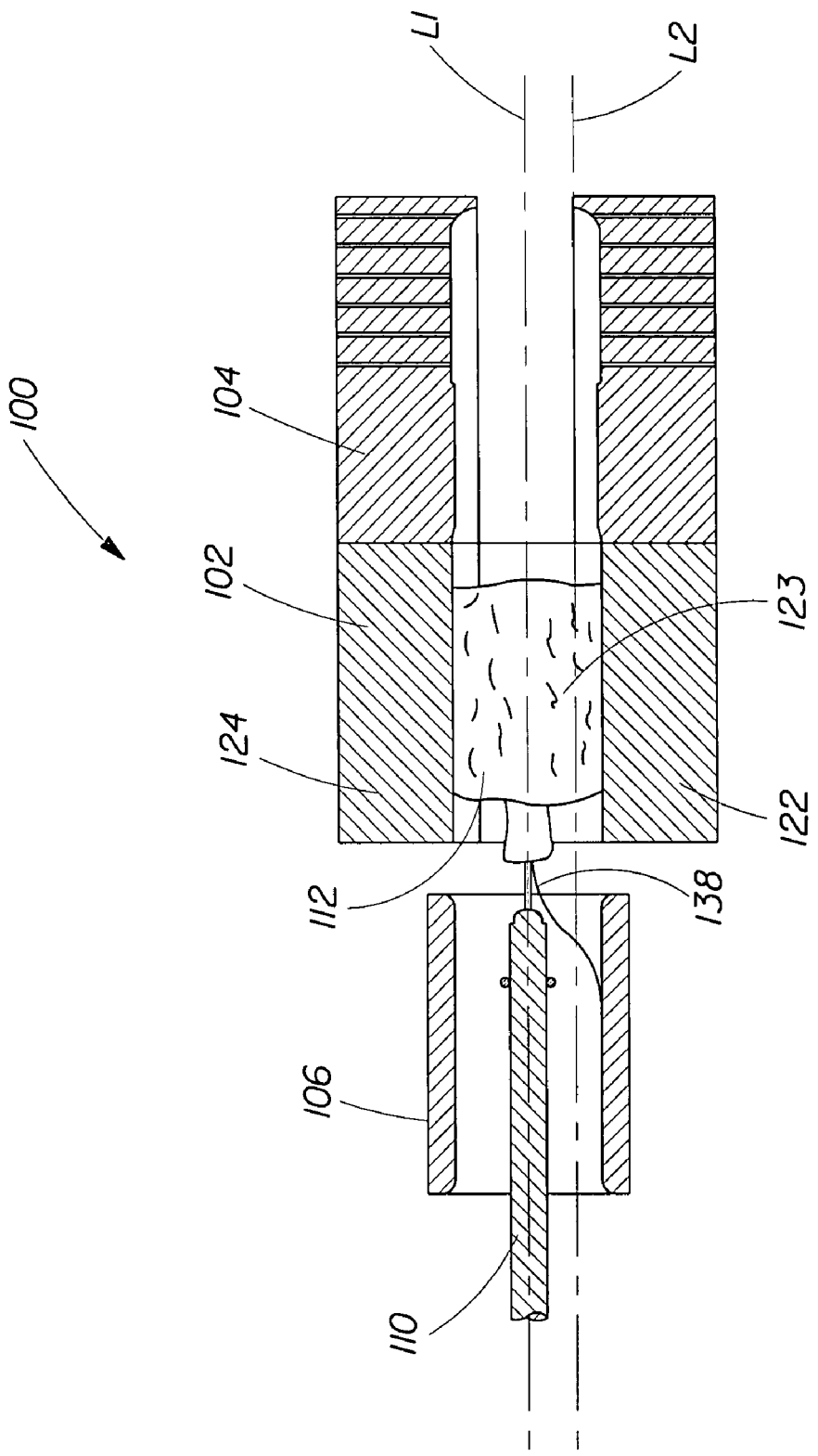
FIG. 16 is a simplified longitudinal cross-sectional view of the embodiment 100 of FIG. 15, showing a transfer member being detracted from the pledget.

FIG. 16 is a simplified longitudinal cross-sectional view of the embodiment 100 of FIG. 10 showing the transfer member 110 being retracted from the pledget 112 with the pledget 112 loaded in the compression mold 102. It should be noted that the detraction of the transfer member from the pledget 112 may be done to detract the needle(s) 138 from the pledget 112 prior to the compression of the pledget 112. However, other contemplated embodiments of the transfer member 110 may allow the needle(s) 138 to move inside the transfer member 110 to protrude from or hide inside the transfer member 110, thus eliminating the need for the retraction of the transfer member 110.

It should be also noted that other contemplated embodiments of the split compression and stabilization molds 102 and 104, respectively, may include both moving mold members, in contrast to embodiments including a moving mold member and a fixed mold member. When both moving mold members are employed, the transfer member 110 does not need to move in the direction R for closing and opening of the molds.

Figure 17:
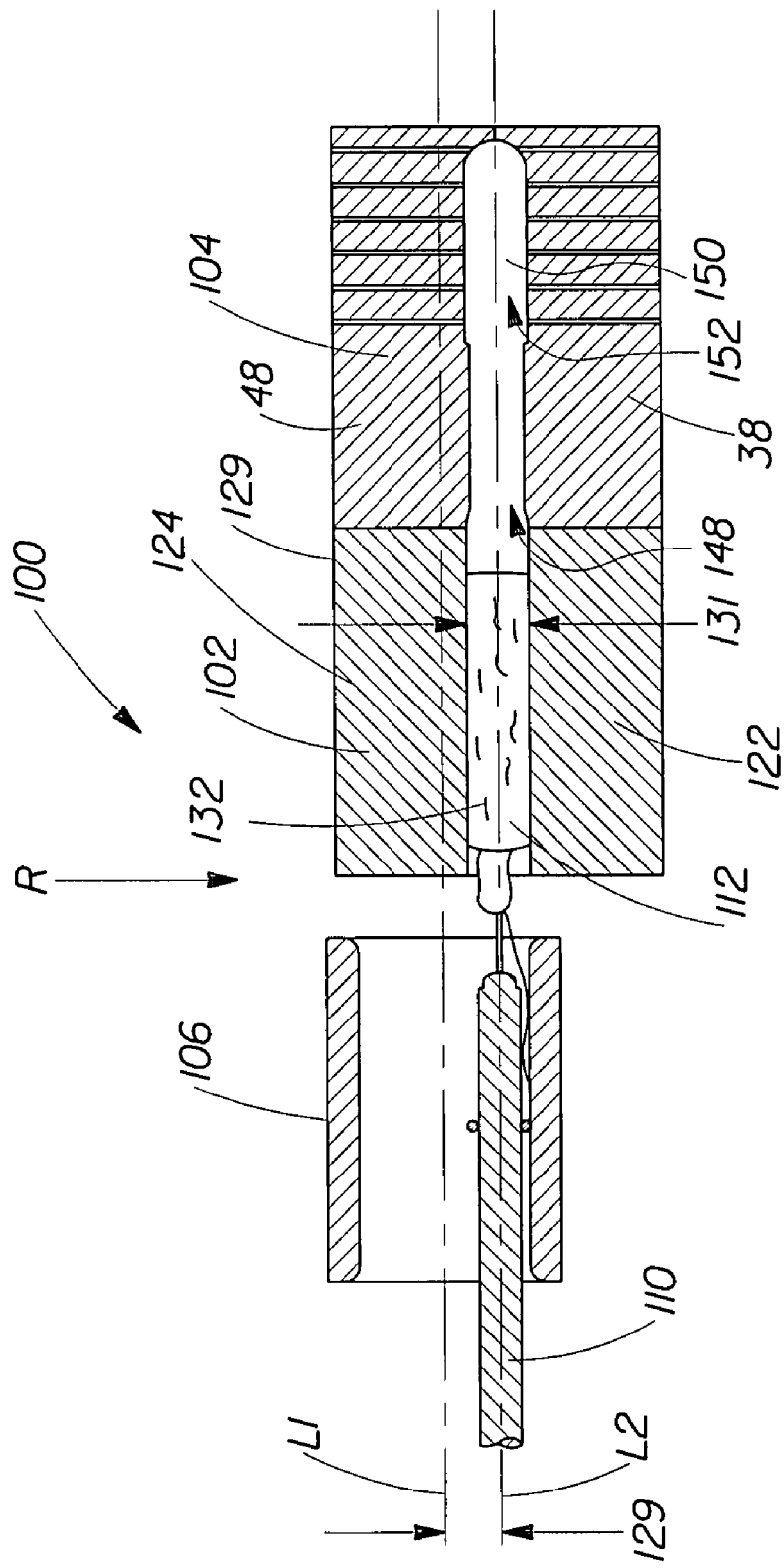
FIG. 17 is a simplified longitudinal cross-sectional view of the embodiment 100 of FIG. 16, showing the pledget being compressed into a compressed pledget in the compression mold.

FIG. 17 is a simplified longitudinal cross-sectional view of the embodiment 100 of FIG. 10, showing the pledget 112 being compressed into a compressed pledget 132 in the compression mold 102 when the compression mold 102 is in the closed position 129. In the closed position 129, the compression mold 102 has an inside dimension 131 that can be any dimension suitable for compressing the pledget 112 into a desired compressed dimension. For example, in one embodiment of the invention, the inside dimension 131 is compressed to about 12.5 mm. The pledget 112 may be partially compressed in compression mold 102, thereby forming the compressed pledget 132, and the compressed pledget 132 is further compressed or compacted when the transfer member 110 loads the compressed pledget 132 into the stabilization mold 104, as described below.

The closed position 129 may be accomplished by moving the first compression mold member 122 in the direction R toward the second compression mold member 124. However, as noted above, other contemplated embodiments of the present invention can include both moving mold members. During the closing of the compression mold 102, the pledget 112 undergoes a radial compression in the direction R, reducing the radial dimension of the pledget 112 to the inside dimension 131, which may be any suitable dimension, for example, about 12.5 mm. Thus, in one example, the first compression mold member 122 moved radially from about 40.5 mm to about 12.5 mm, resulting in a total movement of about 28 mm.

As shown in FIG. 17, the transfer member 110 also moved in the direction R to become aligned along a second longitudinal centerline L2 aligned with the closed position 129 of the compression mold 102. The distance between the first longitudinal centerline L1 and the second longitudinal centerline L2 is a dimension 129, which may be about half of the radial movement of the first compression mold member 122. For example, in the particular example above, when the first compression mold member 122 moves about 28 mm, the transfer member 112 moves the distance 129 of about 14 mm.

Figure 18:
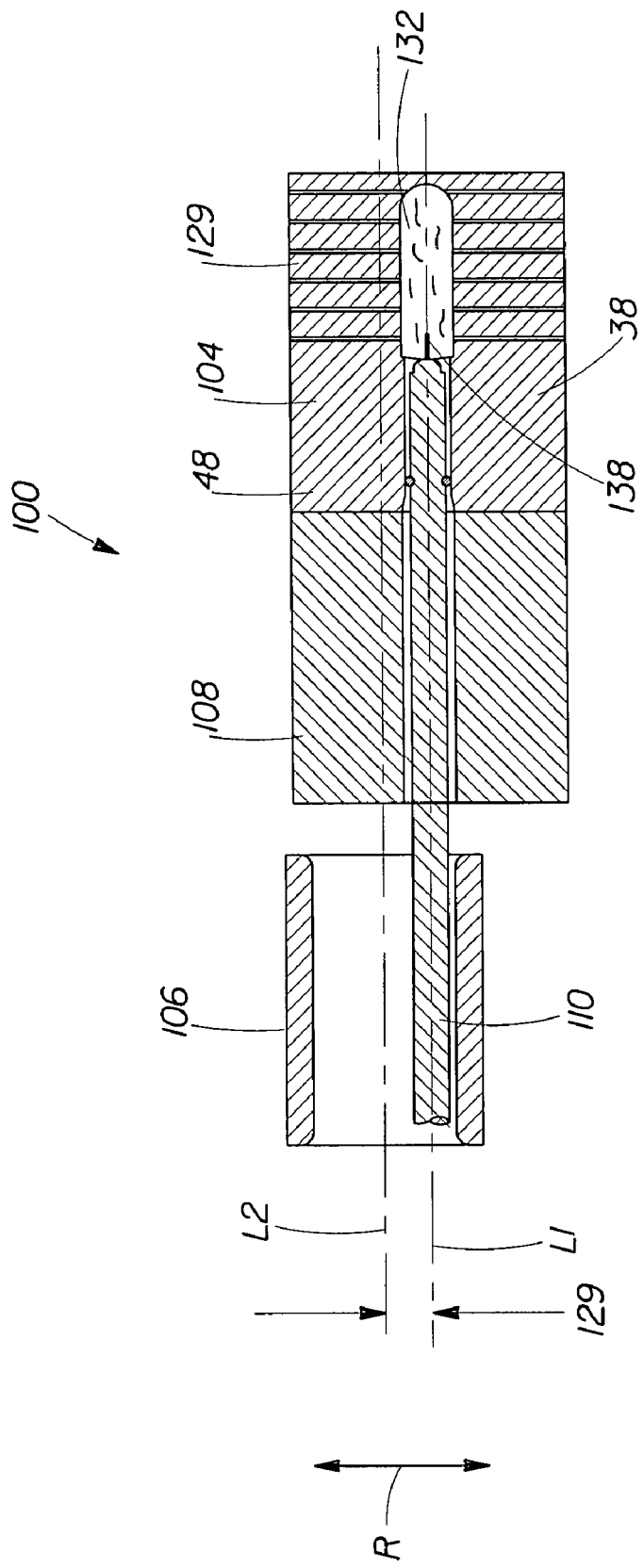
FIG. 18 is a simplified longitudinal cross-sectional view of the embodiment 100 of FIG. 17, showing the compressed pledget being loaded into the stabilization mold.

FIG. 18 is a simplified longitudinal cross-sectional view of the embodiment 100 of FIG. 10, showing the compressed pledget 132 being loaded into the stabilization mold 104 by the transfer member 110. The transfer member 110 loads the compressed pledget 132 into the inner cavity 150, best seen in FIG. 17, of the stabilization mold 104 by advancing the compressed pledget 132 axially along the longitudinal axis of the stabilization mold, through an inlet region 148 of the stabilization mold 104 and into the inner cavity 150 of the stabilization mold 104 through an open proximal end 152 of the inner cavity 150. The advancing transfer member 110 provides sufficient force to the compressed pledget 132 for the compressed pledget 132 to fill an inner cavity 150 of the stabilization mold 104.

Figure 26:
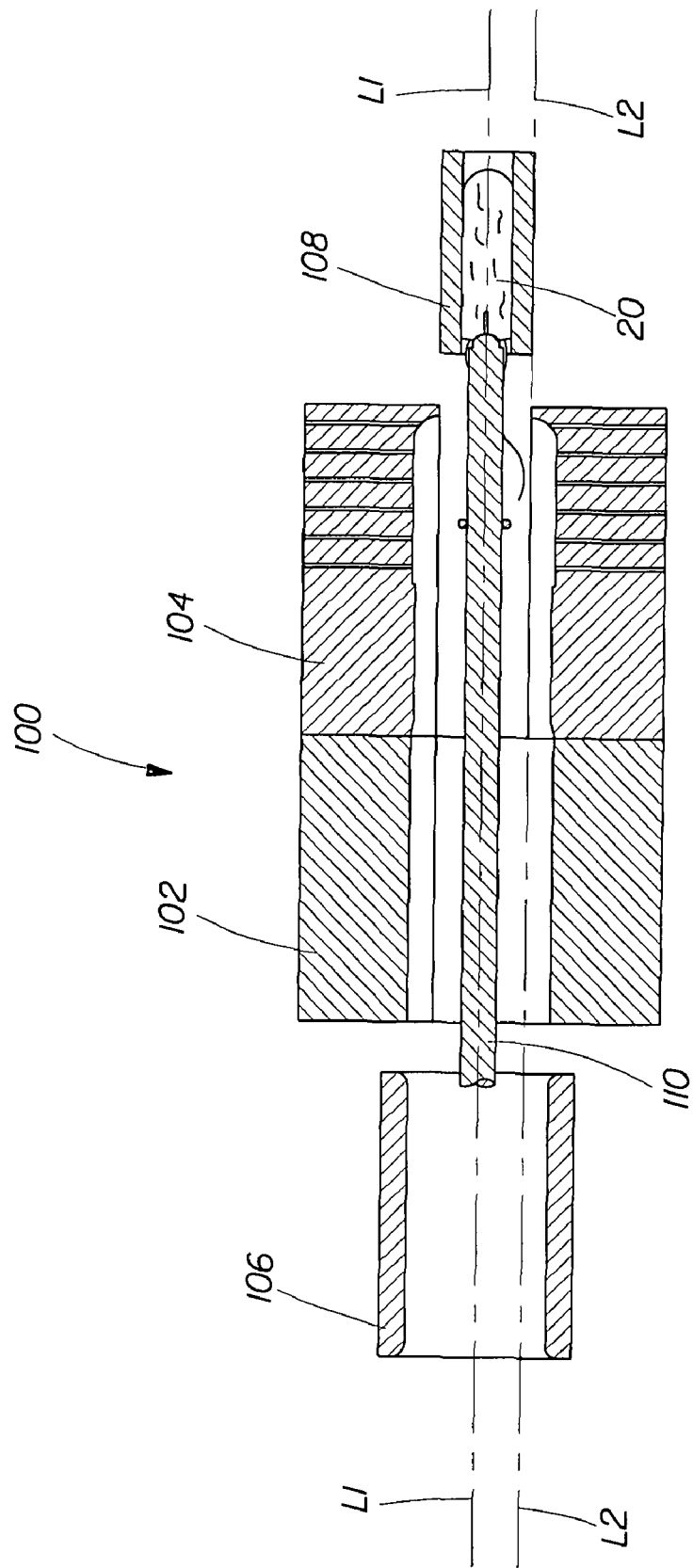
FIG. 26 is a simplified longitudinal cross-sectional view of the embodiment 100 of FIG. 25, showing the stabilized product being loaded into a discharge carrier by the transfer member.

As noted above, the transfer member 110 may include at least one needle 138 extending from the transfer member 110 longitudinally. The needle(s) 138 can have a relatively sharp point to provide penetration of the needle(s) 138 into the compressed pledget 132 without damaging the compressed pledget 132. The needle(s) 138 can be of any suitable diameter, for example, between about 1-2 mm, extending from the transfer member 110 at any suitable length sufficient to hold the compressed pledget 132, as shown in FIG. 26, for example, about 12 mm.

Figure 19:
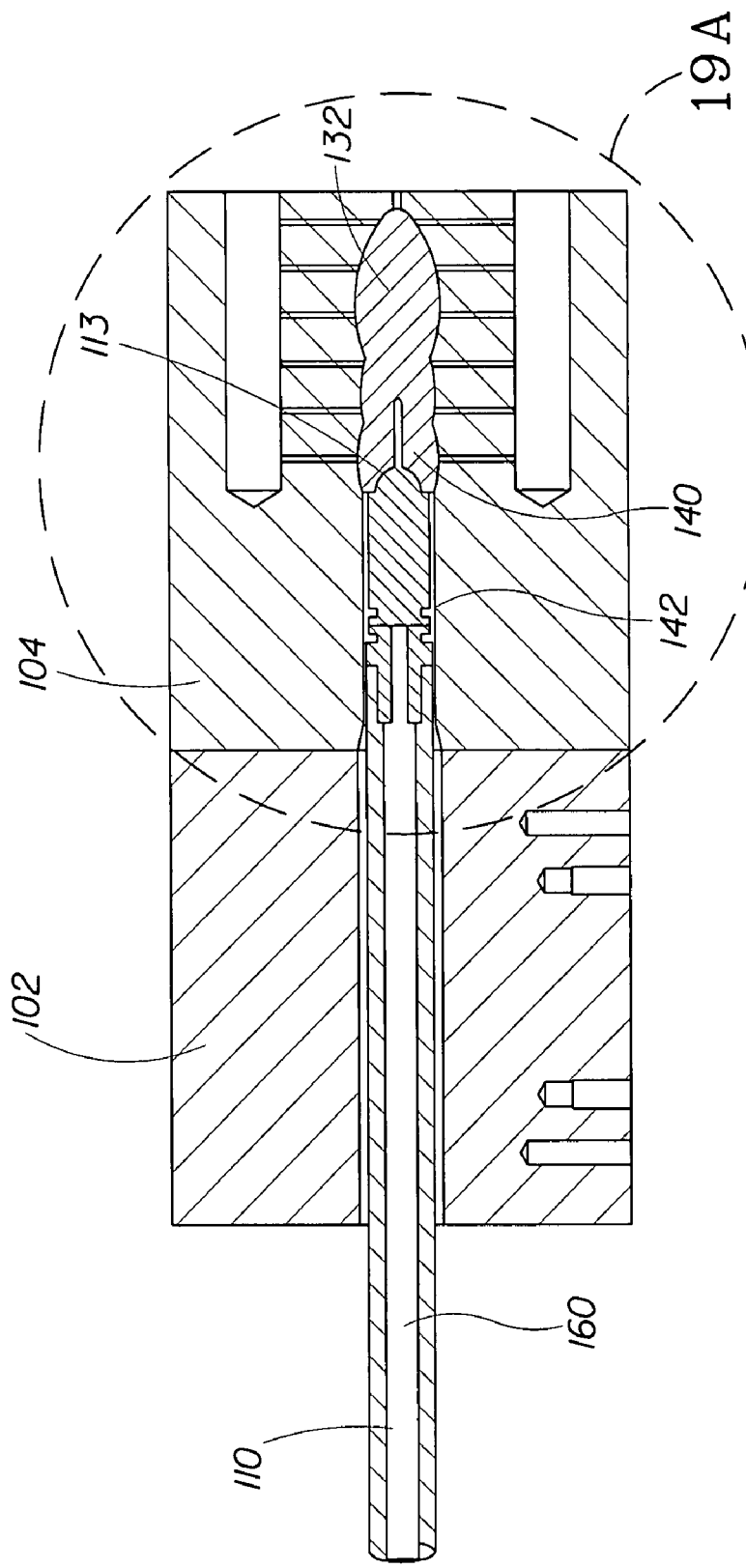
FIG. 19 is a cross-sectional view of a stabilization mold and a transfer member with a compressed pledget in the stabilization mold in one embodiment where the transfer member includes an expandable seal.

FIG. 19 is a cross-sectional view of one embodiment of the transfer member 110, where the transfer member includes an expandable seal 142. Expandable seal 142 can be expanded with the transfer member 110 having advanced the compressed pledget 132 into the stabilization mold 104 and penetrated the compressed pledget 132 inside the stabilization mold 104. The transfer member 110 may include a tip portion 113 formed from a polymer, Such as nylon, or from other suitable materials. The tip portion 113 may be coupled to the transfer member 110 by friction fit, adhesive, or other known means to form a seal therebetween. The end of the tip 113 that drives the compressed pledget 132 into the stabilization mold 104 may be appropriately shaped to form a cavity 140 in the tampon that is suitable for the user's finger to facilitate digital insertion of the product into a body cavity. The tip 113 includes an expandable seal 142 capable of sealing the inner cavity 150 of the stabilization mold 104 to contain the gas that will be injected into the inner cavity 150 of the stabilization mold 104 during the step of stabilization treatment of the tampon, as described below.

Figure 19A:
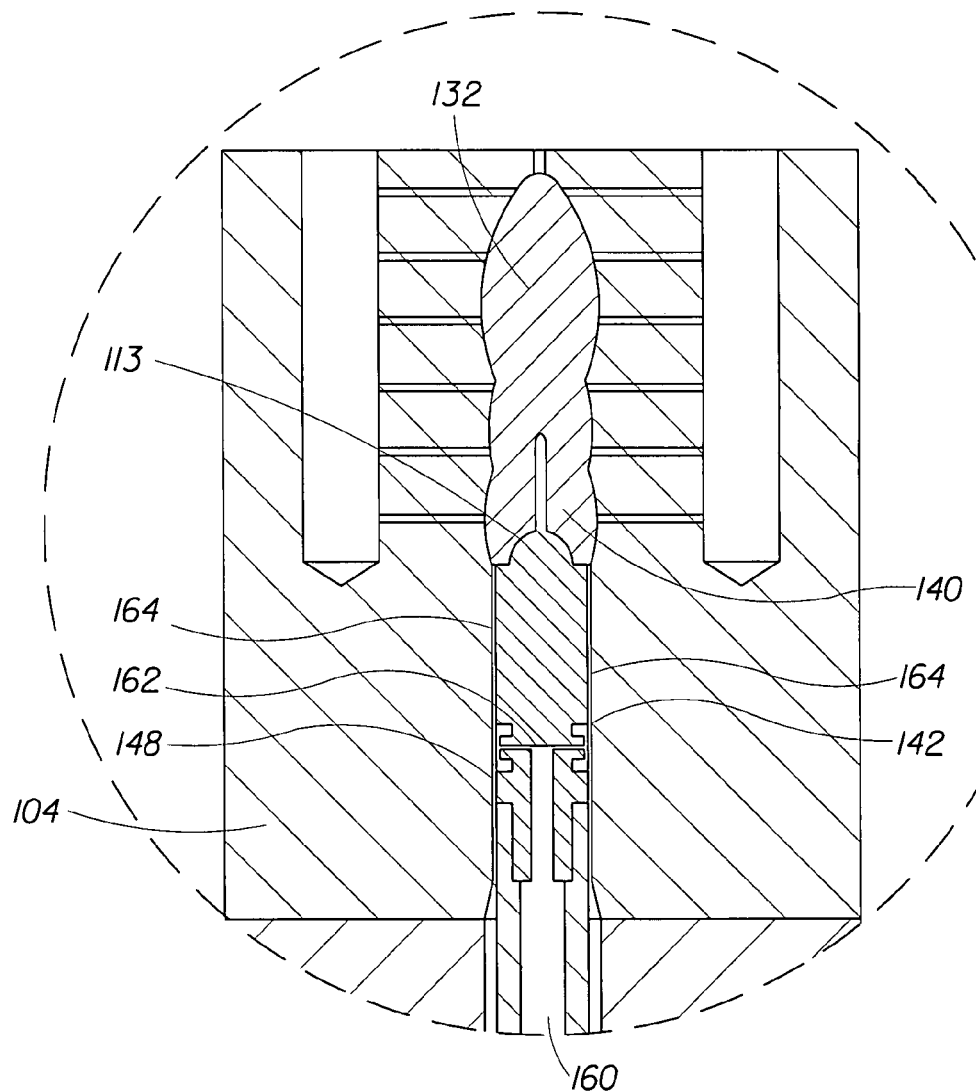
FIG. 19A is a cross-sectional view of the embodiment of the transfer member shown in FIG. 19, where the expandable seal is in a relaxed position.

FIG. 19A is a cross-sectional view of the embodiment of the transfer member 110 shown in FIG. 19, where the transfer member 110 includes an expandable seal 142 in a relaxed position. In the embodiment shown in FIG. 19A, the expandable seal 142 is a gasket surrounding a recess formed in tip 113. The recess may be generally radial, discontinuous, continuous, or formed in any suitable manner. A generally axial channel 160 formed in transfer member 110 extends along the longitudinal axis of the transfer member 110 and partially through the tip 113, as shown in FIGS. 19 and 19A. The axial channel 160 terminates inside the tip 113 and adjoins radial channels 162 formed in tip 113, which extend radially to expandable seal 142. Radial channels 162 may be of any suitable dimension or shape. The dimensions of the channels may be larger than that of the solid structure, ranging from the radial channels 162 being small holes to the radial channels resembling the gaps between the solid spokes of a bicycle wheel. Any suitable number of radial channels 162 may be used. Two radial channels 162 are shown in the embodiment depicted in FIG. 19A, but more radial channels may be provided, or a single radial channel may be provided, or three or more radial channels 162 may be used, leading from the axial channel 160 to the expandable seal 142. In another embodiment, tip 113 may include porous or permeable metal or polymer or the like proximate expandable seal 142 that allows air or other suitable gas to be transmitted from the axial channel 160 to the expandable seal 142, as described below.

The expandable seal 142 operates as a bladder with gas-retaining walls for forming a seal within the stabilization mold 104. Prior to operation, the seal 142 is in a relaxed position, seen in FIG. 19A. In the relaxed position, a gap 164 in the inlet region 148 may be formed between tip 113 and interior walls of the inlet region, allowing air to pass axially along the longitudinal axis of the stabilization mold. The gap 164 results from a diameter of the transfer member tip 113 being not larger than the diameter formed by the cylindrical interior walls of cavity 150. By selecting an appropriate diameter for tip 113, a sufficient gap 164 may be provided that reduces wear and deterioration of the tip 113 and the seal 142 due to friction experienced with the interior walls of cavity 150 when the transfer member is advanced and retracted. The gap 164 further minimizes the likelihood of cutting or deforming a withdrawal cord of the compressed pledget 132 due to insufficient gap when the compressed pledget 132 is advanced into the stabilization mold 104 by transfer member 110.

Figure 19B:
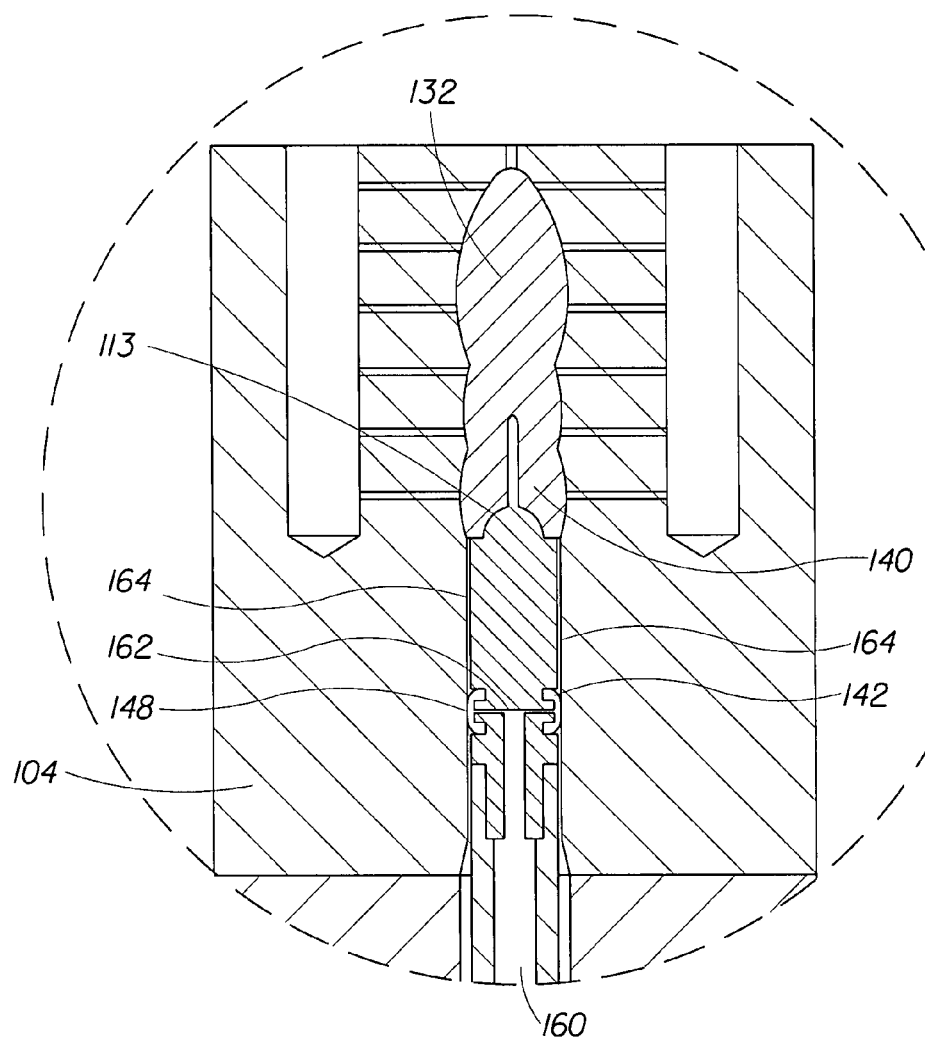
FIG. 19B is a cross-sectional view of the embodiment of the transfer member shown in FIG. 19A, where the expandable seal is in an expanded position.

In operation, when air or other suitable gas is introduced with sufficient pressure into the axial channel 160, the seal inflates to an expanded position, seen in FIG. 19B. The air or other gas is delivered to the axial channel 160 through known means to create a pulse of air or a steady airflow that creates a positive pressure in the axial channel and brings the seal 142 to the expanded position. The seal 142 in the expanded position compresses against interior walls of the inlet region 148 of the stabilization mold 104 to fill a radial segment of the mold, and thereby closes the gap 164 and forms an annular seal with the inlet region 148.

The air pressurization that causes the seal 142 to inflate to the expanded position is maintained during the stabilization, throughout delivery of gas flow to the stabilization mold 104. While the compressed pledget 132 is stabilized in the stabilization mold as described below, the expanded seal 142 contains the gas that is injected into the stabilization mold 104 substantially in the inner cavity 150 and reduces seepage out through the gap 164 along the inlet region of the stabilization mold 104. Other configurations of the expandable seal 142, the inner cavity and the inlet region of the stabilization mold with which the seal is formed, and the means for expanding the seal may be implemented without departing from the spirit and scope of the invention.

Figure 19C:
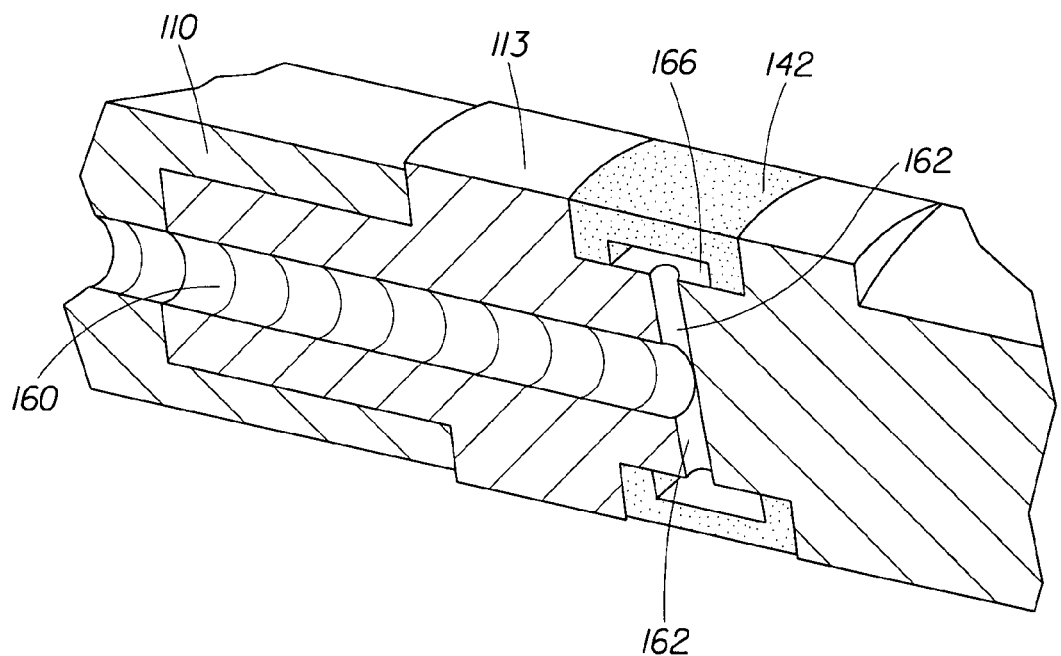
FIG. 19C is a cross-sectional perspective view of the embodiment of the transfer member shown in FIG. 19A, where the expandable seal is in a relaxed position.

FIG. 19C is a cross-sectional perspective view of the embodiment of the transfer member 110 shown in FIGS. 19A and 19B, where the transfer member 110 includes an expandable seal 142 in the relaxed position. The expandable seal 142 may be formed of any suitable material, including rubbers, polymers, plastics, other materials, and combinations of these. The expandable seal 142 also may be formed in any suitable dimension, in which its cross-section is U-shaped, generally round, generally oval, square, rectangular, triangular, trapezoidal, or any other suitable shape. As seen in FIG. 19C, each radial channel 162 may be a cut channel, of any suitable shape and dimension, formed in the body of the tip 113. The expandable seal 142 may be configured to define a recess that forms a gasket chamber 166 inside the seal between the seal and the radial recess in tip 113. The gasket chamber 166 adjoins the radial channels 162 such that air delivered to the axial chamber will pass through to the radial channels 162 and into the gasket chamber 166, thereby causing the seal 142 to expand to the expanded position.

Figure 20:
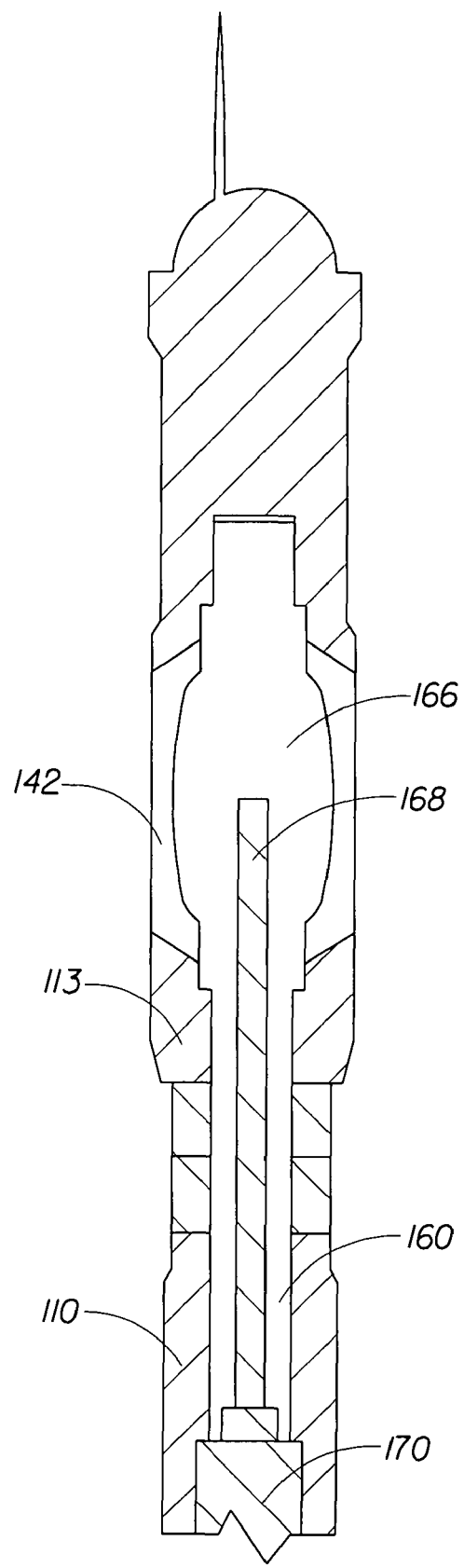
FIG. 20 is a cross-sectional view of another embodiment of the transfer member with an expandable seal in a relaxed position.

FIG. 20 is a cross-sectional view of another embodiment of the transfer member 110 with an expandable seal 142 in a relaxed position. In the embodiment shown in FIG. 20, the expandable seal 142 is a gasket with trapezoidal cross-sections surrounding a radial recess formed in tip 113. The triangular edges of the seal 142 that form the trapezoidal shape and the similarly shaped mating portion of the tip 113 keep the seal circumferentially disposed about the tip 113, even when the seal is in a expanded position. Axial channel 160 is formed in the transfer member 110 and extends partially through the tip 113. A hollow inflation channel 168 is configured in the axial channel 160 along the axis of the tip 113 and is coupled at one end to a base member 170. The inflation channel 168 extends longitudinally along the axial channel 160, and terminates at the other end in a gasket chamber 166 proximate the seal 142. Inflation channel 168 defines an internal channel configured for air to flow therethrough into axial channel 160, thereby filling the axial channel 160 with air. The base member 170 is placed within the axial channel 160 and defines a longitudinally extending bore that may be aligned with the inflation channel 168, thereby allowing air flowing through the longitudinally extending bore of the base member 170 to be transmitted into the inflation channel 168. The inflation channel 168 is coupled to the base member 170 such that the base member bore is sealed to the inflation channel 168, whereby air or another suitable gas that flows into the base member 170 passes into the inflation channel 168. The air passes along the internal channel of the inflation channel 168 and exits the inflation channel 168 in the gasket chamber 166 through an opening at the distal end of the channel proximate the seal 142. Alternatively, a base member 170 with a longitudinally extending bore may be provided without an inflation channel 168, whereby air flowing through the longitudinally extending bore of the base member 170 passes directly into the gasket chamber 166.

In operation, when the air or other suitable gas is introduced with sufficient pressure into the axial channel 160, the air enters the gasket chamber 166 and the seal 142 inflates to an expanded position. The seal 142 in the expanded position compresses against interior walls of the inlet region of the stabilization mold 104 to fill a radial segment of the mold and thereby closes the gap 164 and seals the inner cavity 150. The thickness of expandable seal 142 may be generally consistent, or it may vary. As seen in FIG. 20, the expandable seal 142 is thinner in the middle and thickest at its edges, in which case the expandable seal 142 expands evenly along its middle, thinnest portion. The expandable seal 142 can be returned to a partially or fully unexpanded state to open the gap 164.

Figure 21:
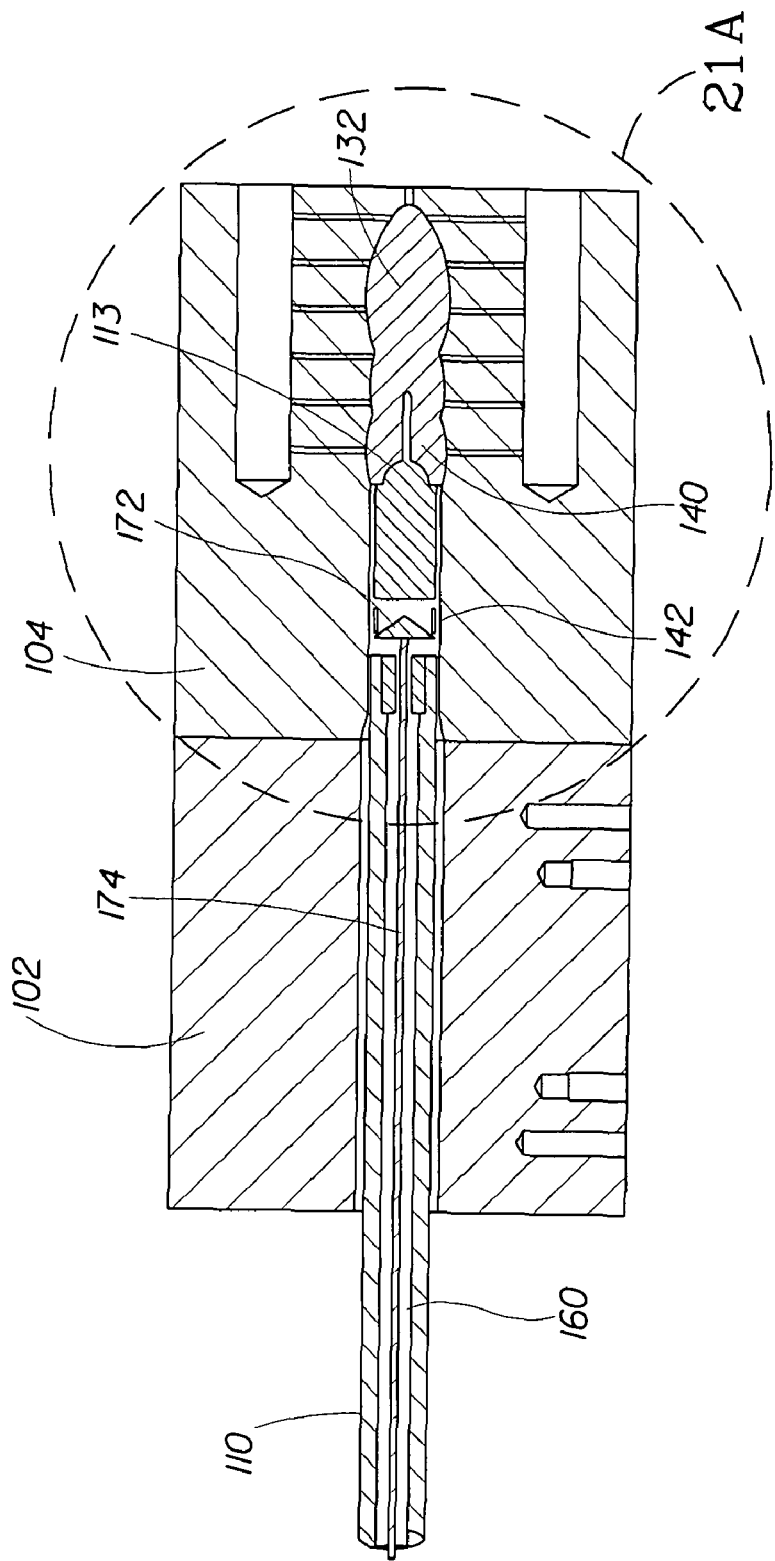
FIG. 21 is a cross-sectional view of a stabilization mold and a transfer member with an expandable seal in a relaxed position in one embodiment where the seal is expanded mechanically.
Figure 21A:
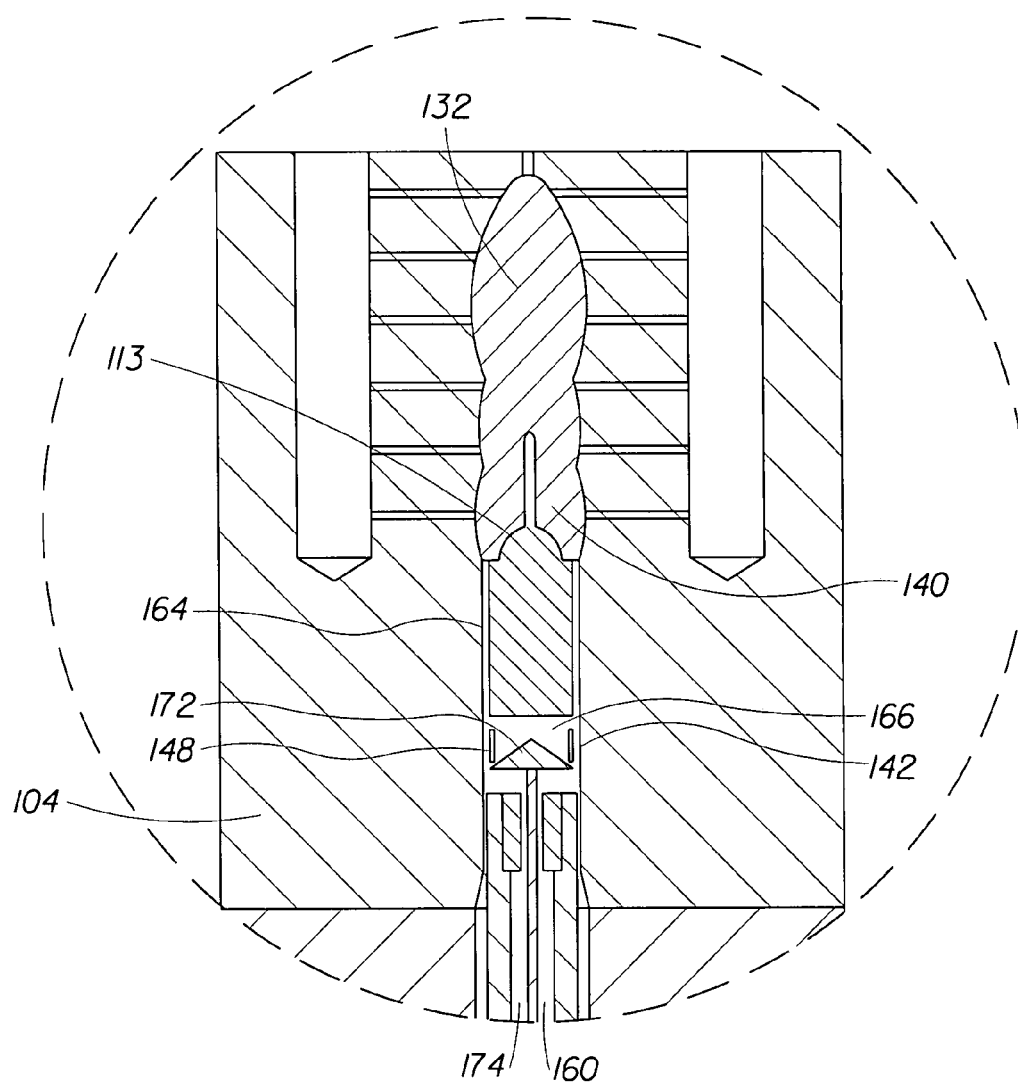
FIG. 21A is a cross-sectional view of the embodiment of the transfer member shown in FIG. 21, where the expandable seal is in a relaxed position.

In certain embodiments, the seal 142 may be expanded by mechanical means. FIG. 21 is a detailed cross-sectional view of yet another embodiment of the transfer member 110 with an expandable seal 142 in a relaxed position, where the seal is expandable by an expansion member 172. Expansion member 172 may be any suitable shape, including conical, tapered, etc. In the embodiment shown in FIG. 21, the expandable seal 142 is a gasket, or other suitable material for creating a seal in the stabilization mold, that surrounds a radial recess formed in tip 113. The expansion member 172 is arranged in the gasket chamber 166 seen in FIG. 21A, and, in the relaxed position, asserts insufficient force on the expandable seal 142 to cause deformation of the seal. The expansion member 172 is coupled with an expansion drive member 174 that is configured in the axial channel 160 along the axis of the tip 113 and extends longitudinally along the axial channel 160. The expansion drive member 174 is arranged to slide back and forth longitudinally within the axial channel 160.

Figure 21B:
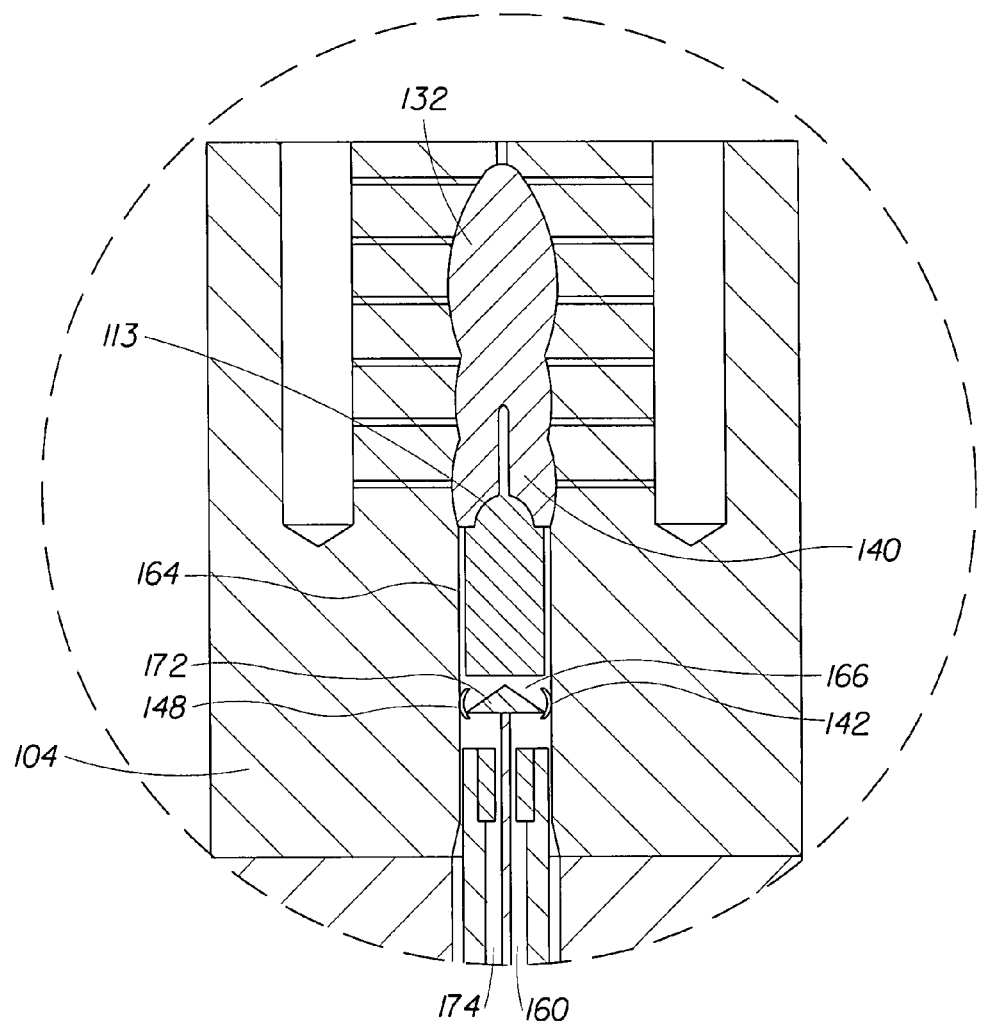
FIG. 21B is a cross-sectional view of the embodiment of the transfer member shown in FIG. 21A, where the expandable seal is in an expanded position.

In operation, when the expansion drive member 174 advances longitudinally towards the stabilization mold 104 with sufficient force, the conical expansion member 172 advances, thereby radially dilating the seal 142 into an expanded position, seen in FIG. 21B. The seal 142 in the expanded position compresses against interior walls of the inlet region 148 of the stabilization mold 104 to fill a radial segment of the mold, and thereby closes the gap 164 and seals the inner cavity 150. Subsequent to the stabilization treatment of the compressed pledget 132 as described below, the expansion drive member 174 is partially or fully retracted to release the dilating force from the conical expansion member 172 on the expandable seal 142, thereby allowing the seal to return to a partially or fully relaxed or unexpanded state.

A driving mechanism may be provided to advance and retract the expansion drive member 174. The driving mechanism may include a gear system, pneumatic or hydraulic systems, or other suitable apparatuses that are capable of being controlled to advance and maintain the expansion drive member 174 with sufficient force.

Figure 21C:
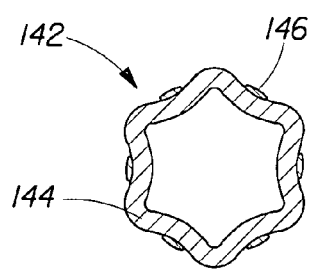
FIG. 21C is a cross section of an expandable seal, taken at its widest point, in accordance with one embodiment.
Figure 21D:
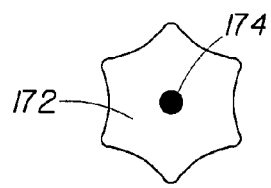
FIG. 21D is a cross section of an expansion member and an expansion drive member in accordance with one embodiment.

In one embodiment, seal 142 includes a deformable perimeter 144 and supportive struts 146 surrounding the deformable perimeter 144, as seen in FIG. 21C. The struts may provide structural connection between the portions of the transfer member tip 113 that are on opposing sides of gasket chamber 166. The struts may be formed from a metal or other material suitable to support the transfer member structure. Conical expansion member 172 may have a similarly shaped cross-section, shown in FIG. 21D, that matches the opening in the center of seal 142, thereby allowing advancement of the expansion member 172 into the seal 142 to expand the deformable perimeter 144, thereby creating a seal with the interior walls of the inlet region 148.

In one embodiment, the transfer member may include a forming end 192 and a driving end 194, as seen in FIG. 22A, where the forming end is situated to receive the driving end in a recess or cavity 196. The expandable seal 142 is arranged about a narrow section of the driving end 194. The driving end is advanced in direct D relative to forming end 192, thereby forcing seal 142 radially outward in direction R, as seen in FIG. 22B, and creating a seal with the interior walls of the inlet region 148 of stabilization mold 104.

Other mechanical means for expanding the seal 142 may implemented without departing from the spirit and scope of the invention. In other embodiments, alternative components such as an expansion wedge member, an expansion bicone member, an expansion conical frustum member, an expansion ellipsoid member, an expansion prolate spheroid member, or other suitably-shaped elements may be implemented rather than conical for expansion member 172. Additional alternatives for expansion member 172 may include a convex expanding member with a drive cylinder that advances into the convex expanding member, or a conical or concave female member defining a groove that expands when receiving a mating male member in the grove. In yet another alternative to expansion member 172, a planar expansion plate 180 may be provided that is driven by a control rod in a twisting direction that the expansion plate to open radially outward.

Referring to FIG. 23A, expansion plate 180 is situated inside expandable seal 142 and is arranged atop rotatable expansion drive member 184. The expansion plate 180 includes a plurality of aperture plate segments 182, seen in FIG. 23D, that may be rotated into open and closed positions by expansion drive member 184. FIG. 23B shows expansion plate 180 in a closed position, where the aperture plate segments are collapsed. Expansion drive member 184 may be rotated in direction A to drive expansion plate 180 into an open position. FIG. 23C shows expansion plate 180 in an open position, where the aperture plate segments have been expanded by rotatable expansion drive member 184 thereby filling inlet region 148 of the stabilization mold 104 and creating a seal between expandable seal 142 and an interior wall of the mold 104.

Figure 24:
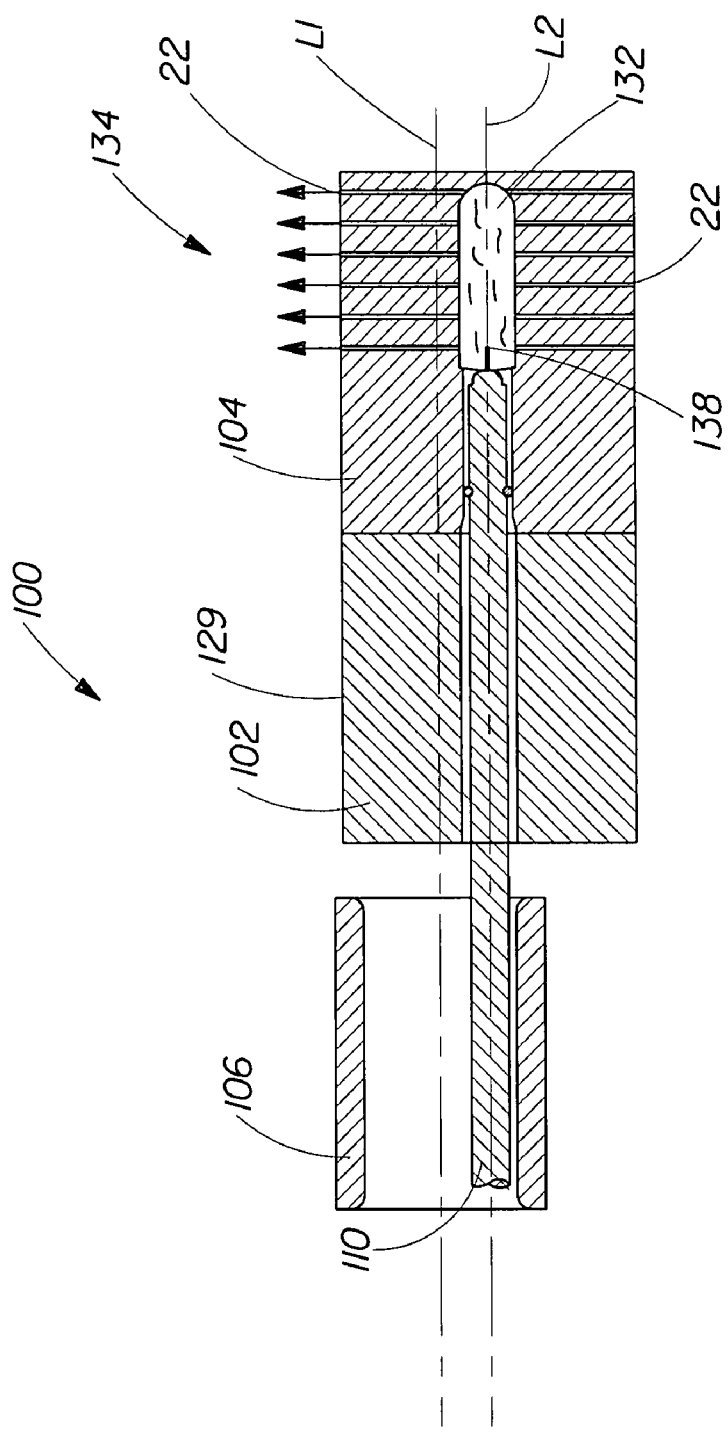
FIG. 24 is a simplified longitudinal cross-sectional view of the embodiment 100 of FIG. 18, showing the compressed pledget being subjected to a gas flow in the stabilization mold to form a stabilized product.

FIG. 24 is a simplified longitudinal cross-sectional view of the embodiment 100 of FIG. 18, showing the compressed pledget 132 being subjected to a gas flow 134 provided through at least one pore 22 of the stabilization mold 104 to form a stabilized tampon 20. The transfer member 110 is aligned with the second longitudinal centerline L2 aligned with the closed position 129 of the stabilization mold 104. The process conditions suitable for stabilizing the compressed pledget 132, including materials, gases, temperature, humidity, time, and the like, are disclosed above. Specifically, with respect to the temperature of the stabilizing mold 104, the stabilizing mold 104 may be maintained at elevated temperature of about 50° C. to about 150° C., or of about 100° C. to about 130° C., to prevent condensation of a gas, for example, a steam, inside the stabilization mold 104. The desired temperature of the stabilization mold 104 can be provided by any suitable means including, for example, electric cartridge heaters.

During the supplying of the gas flow 134, the gas flow 134 is supplied through a pressurized side of the stabilization mold 104 and vented through a venting side of the stabilization mold into the atmosphere to provide a flow of the gas through the compressed pledget inside the stabilization mold. The gas flow and venting can range from about 0.5 s to about 5 s, or from about 0.5 s to about 1.5 s. The gas flow 134 through the stabilization mold 104 is controlled by the expanded seal 142, which plugs the inlet region 148 of the stabilization mold 104, thereby causing the gas flow to be directed through the one or more pores 22 with little or no seepage through the proximal end of the mold. Upon completion of the stabilization process, the expandable seal 142 may be returned to the relaxed position. It should be noted that the above method of sealing the inner cavity 150 of the stabilization mold 104 with an expandable seal during the stabilization process can be applicable for stabilizing pledgets not only in a mold utilizing a gas flow, but also for any type of a stabilization mold, for example, molds utilizing conductive heating, microwave heating, and the like.

Figure 25:
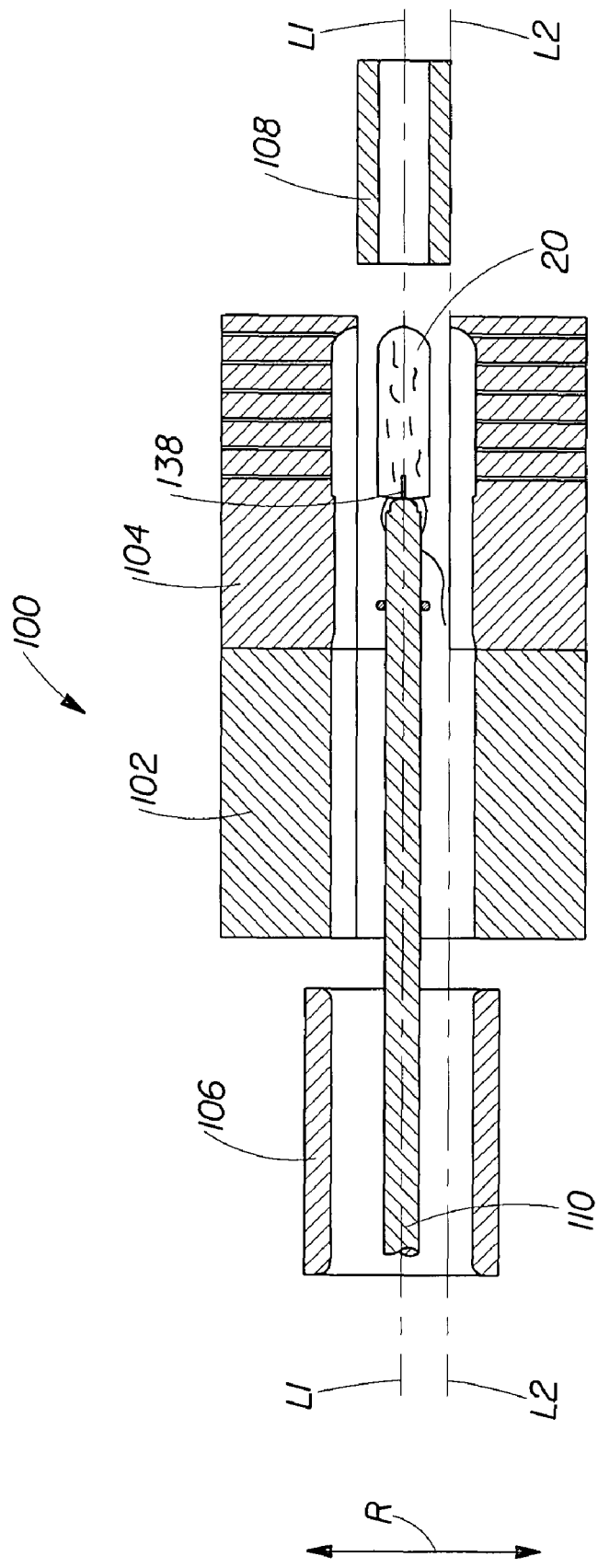
FIG. 25 is the a simplified longitudinal cross-sectional view of the embodiment 100 of FIG. 24, showing the stabilized product held by the transfer member inside the open stabilized mold.

FIG. 25 is a simplified longitudinal cross-sectional view of the embodiment 100 of FIG. 10, showing the stabilized tampon 20 being stripped from the inner surface of the stabilization mold 104 and held by the needle(s) 138 of the transfer member 110 inside the stabilization mold 104 when the stabilization mold 104 is returned to the open position 128 (i.e., aligned with the first longitudinal centerline L1) and the transfer member 110 is returned to be aligned with the first longitudinal centerline L1.

As noted above, the transfer member 110 may include at least one needle 138 extending from the transfer member 110 longitudinally. The needle(s) 138 are capable of penetrating into the stabilized product 20 to enable a subsequent discharge of the stabilized product 20 from the stabilization mold 104. The number of needles 138 can include any suitable number, such as two or more, which would prevent turning of the tampon around a single needle around a longitudinal direction of the product 20.

The needle(s) 138 can have a relatively sharp point to provide penetration of the needle(s) 138 into the stabilized product 20 without damaging the stabilized product 20. The needle(s) 138 can be of any suitable diameter, for example, between about 1-2 mm, extending from the transfer member 110 at any suitable length sufficient to hold the stabilized product 20, for example, about 12 mm.

It should be noted that the above method of unloading stabilized products 20 by the use of a transfer member having one or more needles can be applicable for unloading products not only from a stabilization mold utilizing a gas flow, but also for any type of a stabilization mold, for example, molds utilizing conductive heating, microwave heating, and the like.

FIG. 26 is a simplified longitudinal cross-sectional view of the embodiment 100 of FIG. 10, showing the stabilized product 20 being loaded into the product discharge carrier 108 by the transfer member 110. The transfer member 110 remains aligned with the first longitudinal centerline L1.

Figure 27:
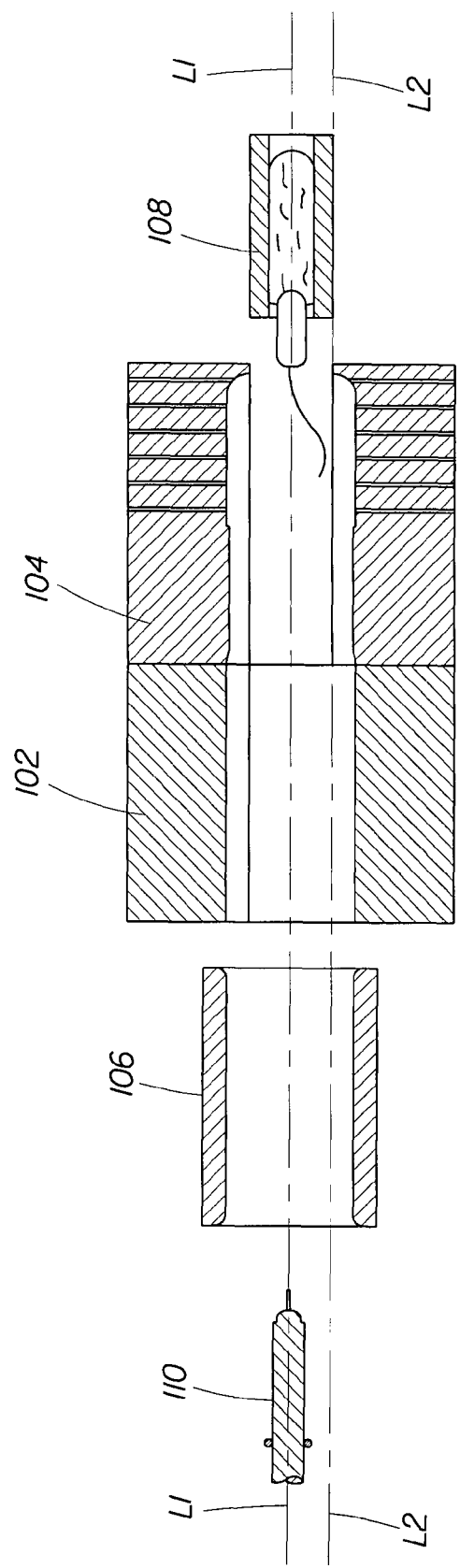
FIG. 27 is a simplified longitudinal cross-sectional view of the embodiment 100 of FIG. 26, showing the transfer member retracted from the stabilized product.

FIG. 27 is a simplified longitudinal cross-sectional view of the embodiment 100 of FIG. 10, showing the transfer member 110 being retracted from the stabilized product 20 and aligned with the first longitudinal centerline L1. The stabilized product 20 remains in the product discharge carrier 108 for further transferring to downstream processing, such as, for example, wrapping and packaging.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for stabilizing a product from a pledget, comprising the steps of:
providing a pledget disposed in a compression mold;
compressing said pledget in said compression mold to form a compressed pledget;
unloading said compressed pledget from said compression mold and loading said compressed pledget into a stabilization mold by a transfer member, said transfer member having an expandable portion and said stabilization mold having an interior surface defining an interior cavity;
expanding said expandable portion in said interior cavity to form a generally annular surface engagement with said interior surface of said stabilization mold;
stabilizing said compressed pledget in said stabilization mold to form a stabilized product, wherein said expandable portion of said transfer member remains expanded during the step of stabilizing said product; and
unloading said stabilized product from said stabilization mold.

2. The process according to claim 1, wherein said expandable portion is a gasket fitted circumferentially around said transfer member.

3. The process according to claim 1, further including the step of returning the expandable portion to an unexpanded state.

4. The process according to claim 1, wherein said transfer member comprises an axial channel extending longitudinally therein and configured to transfer a gas therethrough to said expandable portion.

5. The process according to claim 4, wherein said stabilized product is a tampon.

6. The process according to claim 1, wherein the step of expanding said expandable portion comprises mechanically dilating said expandable portion in an outward radial direction.

7. The process according to claim 6, wherein said transfer member includes a member for engaging and dilating said expandable portion.

8. The process according to claim 1, wherein the step of stabilizing includes applying a gas to said compressed pledget in said stabilization mold, and wherein said annular surface engagement substantially retains said gas from leaking between said transfer member and said stabilization mold during the step of stabilizing.

9. The process according to claim 1, wherein step of stabilizing includes applying microwave heat to said compressed pledget in said stabilization mold.

10. A process for producing a stabilized product from a compressed pledget, comprising the steps of:
providing a pledget;
providing a transfer member, said transfer member having an expandable portion;
providing a mold, said mold having an interior surface defining an interior cavity;
pushing said pledget into said mold with said transfer member such that said expandable portion is within said interior cavity,
expanding said expandable portion of said transfer member to form a seal with said interior surface of said mold; and
stabilizing said pledget, while said expandable portion of said transfer member remains expanded.

11. The process according to claim 10, wherein said expandable portion is a gasket fitted circumferentially around said transfer member.

12. The process according to claim 10, wherein said transfer member defines an axial channel extending longitudinally therein and configured to transfer a gas therethrough to said expandable portion.

13. The process according to claim 12, wherein said axial channel is connected to at least one radial channel extending radially from said axial channel to said expandable portion and configured to transfer a gas from said axial channel in an outward radial direction to said expandable portion.

14. The process according to claim 12, wherein the step of expanding said expandable portion comprises delivering said gas into said axial channel, thereby creating an outward radial deformation of the expandable member and forming said seal with said interior surface.

15. The process according to claim 10, wherein the step of expanding said expandable portion comprises mechanically dilating said expandable portion in an outward radial direction.

16. The process according to claim 10, wherein the step of stabilizing includes applying a gas to said pledget in said mold.

17. The process according to claim 16, wherein said seal substantially retains said gas from leaking between said transfer member and said mold during the step of stabilizing.

18. A stabilization apparatus for stabilizing a compressed tampon pledget, the apparatus comprising:
 a stabilization mold, said mold having an interior surface defining an interior cavity, and said interior cavity configured for receiving and stabilizing a tampon pledget; and
 a transfer member having a tip configured to advance said tampon pledget into said stabilization mold and an expandable portion fitted circumferentially around said tip and configured to enter said interior cavity and expand in an outward radial direction to form a seal with said interior surface of said stabilization mold.

19. The apparatus according to claim 18, wherein the seal is an annular seal between said expandable portion and said interior surface of the stabilization mold.

20. The apparatus according to claim 18, wherein said transfer member comprises an axial channel extending longitudinally therein and configured to transfer a gas therethrough to said expandable portion.

\* \* \* \* \*

UNITED STATES PATENT AND TRADEMARK OFFICE
CERTIFICATE OF CORRECTION

PATENT NO. : 7,736,572 B2  Page 1 of 1
APPLICATION NO. : 11/595322
DATED : June 15, 2010
INVENTOR(S) : Steven Ray Gilbert et al.

It is certified that error appears in the above-identified patent and that said Letters Patent is hereby corrected as shown below:

Title Page

*Primary Examiner*- delete "Khnh" and insert -- Khanh --.

Signed and Sealed this
Twenty-second Day of March, 2011

David J. Kappos
*Director of the United States Patent and Trademark Office*